United States Patent [19]

Frank

[11] Patent Number: 5,401,720
[45] Date of Patent: Mar. 28, 1995

[54] ALKYL TETRALIN ALDEHYDE COMPOUNDS

[75] Inventor: Walter C. Frank, Holland, Pa.

[73] Assignee: Union Camp Corporation, Princeton, N.J.

[21] Appl. No.: 184,584

[22] Filed: Jan. 21, 1994

Related U.S. Application Data

[63] Continuation-in-part of Ser. No. 80,078, Jun. 18, 1993, Pat. No. 5,292,719.

[51] Int. Cl.⁶ .................................................. A61K 7/46
[52] U.S. Cl. ................................... 512/16; 568/440; 568/441
[58] Field of Search ................... 568/440, 441; 512/16

[56] References Cited

U.S. PATENT DOCUMENTS

| | | | |
|---|---|---|---|
| 2,800,501 | 7/1958 | Carpenter et al. | 568/440 |
| 2,800,511 | 7/1959 | Carpenter | 260/599 |
| 2,897,237 | 7/1959 | Carpenter | 260/592 |
| 3,244,751 | 4/1966 | Theimer et al. | 260/592 |
| 3,246,044 | 4/1966 | Wood et al. | 260/668 |
| 3,278,621 | 10/1966 | Stoffberg et al. | 568/440 |
| 3,278,622 | 10/1966 | Stofberg et al. | 260/668 |
| 3,379,785 | 4/1968 | Kahn | 260/668 |
| 3,400,159 | 9/1968 | Theimer et al. | 260/592 |
| 3,442,640 | 5/1969 | Wood et al. | 71/124 |
| 3,509,215 | 4/1970 | Wood et al. | 260/592 |
| 3,856,875 | 12/1974 | Wood et al. | 260/668 |
| 4,162,256 | 7/1979 | Sprecker et al. | 260/345 |
| 4,284,818 | 8/1981 | Sato et al. | 568/323 |
| 4,352,748 | 10/1982 | Traas et al. | 252/522 |
| 4,406,828 | 9/1983 | Gozenbach et al. | 252/522 |
| 4,466,908 | 8/1984 | Sprecker et al. | 252/522 |
| 4,476,040 | 10/1984 | Willis et al. | 252/522 R |
| 4,551,573 | 11/1985 | Cobb | 585/459 |
| 4,605,778 | 8/1986 | Willis et al. | 568/433 |
| 4,767,882 | 8/1988 | Suzukamo et al. | 560/100 |
| 4,877,910 | 10/1989 | Frank | 585/411 |
| 4,877,911 | 10/1989 | Frank | 585/411 |
| 4,877,912 | 10/1989 | Frank | 585/411 |
| 4,877,913 | 10/1989 | Frank | 585/411 |
| 4,877,914 | 10/1989 | Frank | 585/411 |
| 4,877,915 | 10/1989 | Frank | 585/411 |
| 4,877,916 | 10/1989 | Frank | 585/411 |
| 4,880,775 | 11/1989 | Christenson et al. | 512/12 |
| 4,908,349 | 3/1990 | Gozenbach | 512/26 |
| 5,087,770 | 2/1992 | Frank | 568/327 |
| 5,087,785 | 2/1992 | Frank | 585/459 |
| 5,095,152 | 3/1992 | Frank | 568/440 |
| 5,162,588 | 11/1992 | Fehr et al. | 568/328 |
| 5,185,318 | 2/1993 | Fehr et al. | 512/16 |
| 5,206,217 | 4/1993 | Frank | 512/18 |

FOREIGN PATENT DOCUMENTS

| | | |
|---|---|---|
| 301375 | 2/1989 | European Pat. Off. ............ 568/440 |
| 0393742 | 10/1990 | European Pat. Off. . |
| 0405427A2 | 1/1991 | European Pat. Off. . |
| 50-40761 | 4/1975 | Japan . |
| 57-40420 | 4/1982 | Japan . |

OTHER PUBLICATIONS

Muller and D. Lamparsky, *Perfumes, Art, Science and Technology*, Elsevier Science Publishing Co., Inc., New York, N.Y., pp. 254-310 (1991).

Bedoukian, Paul Z., Perfumery and Flavoring Synthetics 3rd Revised Ed., pp. 334-336 (Allured Publishing Corp., Ill. 1986).

Bedoukian, Paul Z., Perfumery and Flavoring Synthetics 2nd Revised Ed., pp. 248-292 (Elsevier Publishing Co. 1967).

Beets, Structure-Activity Relationships in Human Chemoreception, pp. 161-381 (Applied Science Publishers Ltd., London) (1973).

Carey et al., Advanced Organic Chemistry, Part B: Reactions and Synthesis, pp. 383-386 (Plenum Press, N.Y. 1977).

Effenberger, Electrophilic Reagents, *Angewandte Chemie* (Int. Ed. in English), vol. 19, No. 3, pp. 151-230 (1980).

(List continued on next page.)

Primary Examiner—James H. Reamer
Attorney, Agent, or Firm—Woodcock Washburn Kurtz Mackiewicz & Norris

[57] ABSTRACT

The present invention relates, inter alia, to novel alkyl tetralin aldehyde compounds having fragrant musk-like aroma.

23 Claims, No Drawings

OTHER PUBLICATIONS

Fehr et al., New Aromatic Musk Odorants: Design and Synthesis, *Helvetica Chimica Acta*, vol. 72, pp. 1537–1553 (1989).

Godfrey et al., Preparation of Methoxyphenols by Baeyer-Villiger Oxidation of Methoxybenzaldehydes, *J. C. S. Perkin I*, pp. 1353–1354 (1974).

Hannan et al., Synthesis of Bromonaphthoquinones from 1,5-Dimethoxynapthalene, *J. Org. Chem.*, vol. 44, No. 13, pp. 2153–2158 (1979).

Harrison et al., Compendium of Organic Synthetic Methods, pp. 84–85 (Wiley-Interscience, N.Y. 1971).

Hauser et al., Regiospecific Oxidation of Methyl Groups in Dimethylanisoles, *Synthesis*, pp. 723–724 (1987).

Huang et al., A Convenient Synthesis of Aryl Formatest, *J. Chem. Research* (Synop), pp. 292–293 (1991).

Imamoto et al., Cerium(IV) Trifluoromethanesulfonate as a Strong Oxidizing Agent, *Chemistry Letters*, pp. 1445–1446 (1990).

Kreh et al., Selective Oxidations With Ceric Methanesulfonate and Ceric Trifluoromethanesulfonate, *Tetrahedron Ltrs*, vol. 28, No. 10, pp. 1067–1068 (1987).

Lasing et al., Synthetic Steroids. Part IX. A New Route to 19-Nor-steroids, *J. Chem. Soc.* (C), pp. 2915–2918 (1968).

March, J., Advanced Organic Chemistry: Reactions, Mechanisms and Structure, 4th Ed., pp. 1098–1099, 1184–1185 (John Wiley & Sons, N.Y. 1992).

Nikaido et al., Acid-Catalyzed Oxidation of Benzaldehydes to Phenols by Hydrogen Peroxide, *J. Org. Chem.*, vol. 49, pp. 4740–4741 (1984).

Olah et al., Formylating Agents, *Chemical Reviews*, vol. 87, No. 4, pp. 671–686 (1987).

Ohloff et al., Chemical Classification and Structure—Odour Relationships, Perfumes: Art, Science and Technology, pp. 287–330 (Amsterdam 1991).

Rahm et al., Acetone Cyanohydrin, A Convenient Formylation Reagent For Arenes, *Synthetic Communications*, vol. 12, No. 6, pp. 485–487 (1982).

Rieche et al., Aromatic Aldehydes. Mesitaldehyde, *Organic Syntheses*, Collective vol. 5, pp. 49–50 (1973).

Syper, The Baeyer-Villiger Oxidation of Aromatic Aldehydes and Ketones with Hydrogen Peroxide Catalyzed by Selenium Compounds, *Synthesis*, pp. 167–172 (1989).

Syper, Partial Oxidation of Aliphatic Side Chains With Oerium (IV), *Tetrahedron Letters*, No. 37, pp. 4493–4498 (1966).

Syper, Silver (II) As An Oxidant For Organic Compounds, *Tetrahedron Letters*, No. 42, pp. 4193–4198 (1967).

Theimer, Fragrance Chemistry: The Science of the Sense of Smell, pp. 509–534 (Academic Press 1982).

French Patent No. 1,392,804 (as reported in *Chemical Abstracts*, 29-Essential Oils and Cosmetics, vol. 63, p. 6781 (1965)).

Chastrette, Importance of Hydrogen Bonding in the Recognition of Musky Odours, ECRO VIII: Abstracts, pp. 176–177 (1984).

Perrier, *Chem. Ber.*, vol. 33, p. 815 et seq. (1990).

Perrier, *Bull Soc. Chim. France*, pp. 859 et seq. (1904).

ALKYL TETRALIN ALDEHYDE COMPOUNDS

CROSS REFERENCE TO RELATED APPLICATION

This application is a continuation-in-part of patent application U.S. Ser. No. 080,078, filed Jun. 18, 1993, now U.S. Pat. No. 5,292,719, the disclosures of which are hereby incorporated herein by reference in their entirety.

BACKGROUND OF THE INVENTION

The present invention relates, inter alia, to novel alkyl tetralin aldehyde compounds having fragrant musk-like aroma.

Musk fragrances are in great demand for use in various products such as in perfumes, colognes, cosmetics, soaps and others. However, natural musk, which is obtained from the Asian musk deer, is extremely scarce and is quite expensive. Accordingly, fragrance chemists have spent considerable time searching for synthetic products which duplicate or closely simulate this natural musk scent.

As a result of these research efforts, a number of different synthetic musks have been discovered. Among such synthetic compounds is a derivative of 1,1,3,4,4,6-hexamethyl-1,2,3,4-tetrahydronaphthalene (HMT). HMT, for example, is converted to 7-acetyl-1,1,3,4,4,6-hexamethyl-1,2,3,4-tetrahydronaphthalene, to yield a well known musk perfume of the tetralin series. Because of its clean musk fragrance and its ability to retain that fragrance over long periods of time, this compound is of great commercial value as a synthetic musk perfume substitute for the expensive, natural musk perfumes of the macrocyclic ketone series.

New and or better musk aroma compounds are needed to meet the demands of the fragrance industries. The present invention is directed to this, as well as other, important ends.

SUMMARY OF THE INVENTION

The present invention provides novel compounds of the formula [I]:

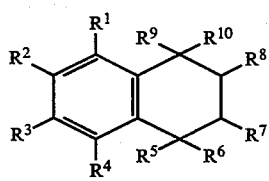

wherein
$R^1$ is —$CH_3$, —$CH_2CH_3$, —$OCH_3$ or —OH,
$R^2$ and $R^3$ are, independently, —H, —$CH_3$, —$CH_2CH_3$, —$OCH_3$, —OH or —C(O)H,
$R^4$ is —H,
$R^5$ is —H, —$CH_3$ or —$CH_2CH_3$,
or $R^4$ and $R^5$ taken together are —$(CH_2)_2$—,
$R^6$ is —$CH_3$ or —$CH_2CH_3$,
$R^7$ is —H, —$CH_3$ or —$CH_2CH_3$,
or $R^6$ and $R^7$ taken together are —$(CH_2)_3$—,
$R^8$ and $R^9$ are, independently, —H, —$CH_3$ or —$CH_2CH_3$, and
$R^{10}$ is —$CH_3$,
provided that (i) one of $R^2$ and $R^3$ is —C(O)H, and one of $R^2$ and $R^3$ is other than —C(O)H,
(ii) no more than one of $R^5$ and $R^9$ is —H,
(iii) no more than one of $R^5$, $R^6$, $R^7$, $R^8$ and $R^9$ is —$CH_2CH_3$,
(iv) when $R^1$ is —$OCH_3$, then $R^2$ and $R^3$ are other than —H or —OH,
(v) when $R^1$ is —OH, then $R^2$ and $R^3$ are other than —OH or —$OCH_3$,
(vi) when $R^1$ is —$CH_3$ or —$CH_2CH_3$, then at least one of $R^7$ and $R^8$ are H,
(vii) when $R^4$ and $R^5$ taken together, are $(CH_2)_2$—, then $R^1$ is —$OCH_3$ or —OH, $R^7$ is —H, and $R^8$ is —H,
(viii) when $R^6$ and $R^7$ taken together are —$(CH_2)_3$—, then $R^1$ is —$OCH_3$ or —OH, and $R^8$ is —H,
(ix) when $R^1$ is —$CH_3$ or —$CH_2CH_3$, then one of $R^2$ and $R^3$ is —$OCH_3$ or —OH,
and
(x) when $R^1$ is —$OCH_3$ or —OH, $R^3$ is —$CH_3$ or —$CH_2CH_3$, and both $R^7$ and $R^8$ are —H, then at least one of $R^5$, $R^6$ and $R^9$ is other than —$CH_3$.

The foregoing compounds possess an active musk aroma having utility in the fragrance industry. The compounds of the invention may be used alone, or in combination with carriers, additional perfumery materials, and/or other ingredients, to provide various products, such as perfumes, colognes, soaps, and cosmetics.

DETAILED DESCRIPTION OF THE INVENTION

As noted above, the present invention is directed to novel musk compounds of the formula [I]:

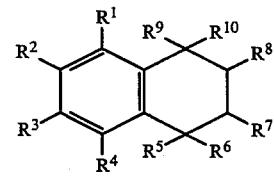

In the above formula [I], the R substituents may be selected as follows: $R^1$ may be selected from the group consisting of —$CH_3$, —$CH_2CH_3$, —$OCH_3$ and —OH; $R^2$ may be selected from the group consisting of —H, —$CH_3$, —$CH_2CH_3$, —$OCH_3$, —OH and —C(O)H; $R^3$ may be selected from the group consisting of —H, —$CH_3$, —$CH_2CH_3$, —$OCH_3$, —OH and —C(O)H; $R^4$ may be —H; $R^5$ may be selected from the group consisting of —H, —$CH_3$ and —$CH_2CH_3$; or $R^4$ and $R^5$, taken together, may be —$(CH_2)_2$—; $R^6$ may be selected from the group consisting of —$CH_3$ and —$CH_2CH_3$; $R^7$ may be selected from the group consisting of —H, —$CH_3$ and —$CH_2CH_3$; or $R^6$ and $R^7$, taken together, may be —$(CH_2)_3$—; $R^8$ may be selected from the group consisting of —H, —$CH_3$ and —$CH_2CH_3$; $R^9$ may be selected from the group consisting of —H, —$CH_3$ and —$CH_2CH_3$; and $R^{10}$ may be —$CH_3$.

As the above indicates, the compound of formula [I] may be a bicyclic compound, where $R^4$ and $R^5$ are other than —$(CH_2)_2$—, and $R^6$ and $R^7$ are other than —$(CH_2)_3$—. The compound of formula [I] may alternatively be a tricyclic compound by virtue of $R^4$ and $R^5$ being taken together as —$(CH_2)_2$—, such as a compound of the formula [II]:

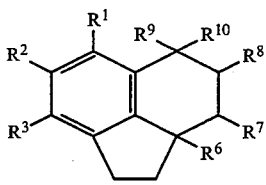

Similarly, the compound of formula [I] may alternatively be a tricyclic compound by virtue of $R^6$ and $R^7$ being taken together as $-(CH_2)_3-$, such as a compound of the formula [III]:

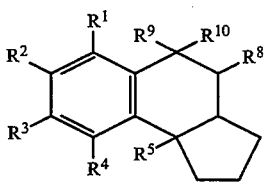

The foregoing selection of R substituents should, however, be made with the following qualifications in mind: that one of $R^2$ and $R^3$ is $-C(O)H$, and the other of $R^2$ and $R^3$ is other than $-C(O)H$; that no more than one of $R^5$ or $R^9$ is $-H$; that no more than one of $R^5$, $R^6$, $R^7$, $R^8$ or $R^9$ is $-CH_2CH_3$; that when $R^1$ is $-OCH_3$, then $R^2$ and $R^3$ are both other than $-H$ or $-OH$; that when $R^1$ is $-OH$, then $R^2$ and $R^3$ are both other than $-OH$ or $-OCH_3$; that when $R^1$ is $-CH_3$ or $-CH_2CH_3$, then one or both of $R^7$ and $R^8$ are H; that when $R^4$ and $R^5$, taken together, are $-(CH_2)_2-$ (that is, a tricylic compound, where the third ring structure is at the $R^4$ and $R^5$ position), then $R^1$ is $-OCH_3$ or $-OH$, $R^7$ is $-H$, and $R^8$ is $-H$; that when $R^6$ and $R^7$, taken together, are $-(CH_2)_3-$ (that is, a tricyclic compound, where the third ring structure is at the $R^6$ and $R^7$ position), then $R^1$ is $-OCH_3$ or $-OH$, and $R^8$ is $-H$; that when $R^1$ is $-CH_3$ or $-CH_2CH_3$, then one of $R^2$ and $R^3$ is $-OCH_3$ or $-OH$; and that when all of the following is true $-R^1$ is $-OCH_3$ or $-OH$, $R^3$ is $-CH_3$ or $-CH_2CH_3$, and both $R^7$ and $R^8$ are $-H-$then at least one of $R^5$, $R^6$ and $R^9$ is other than $-CH_3$.

For reasons of their fragrance characteristics, synthesis advantages, formulation benefits, and/or other values, the following are preferable classes of compounds within the scope of Formula [I]:

Compounds of Formula [I] wherein $R^1$ is $-CH_3$, $-OH$ or $-OCH_3$;

Compounds of Formula [I] wherein $R^2$ is $-C(O)H$;

Compounds of Formula [I] wherein $R^3$ is $-CH_3$ or $-CH_2CH_3$;

Compounds of Formula [I] wherein $R^1$ is $-OH$ or $-OCH_3$, $R^2$ is $-C(O)H$, $R^3$ is $-CH_3$ or $-CH_2CH_3$, $R^4$ is $-H$, $R^5$ is $-CH_3$, $R^6$ is $-CH_3$, $R^7$ is $-H$ or $CH_3$, $R^8$ is $-H$ or $-CH_3$, $R^9$ is $-CH_3$, and $R^{10}$ is $-CH_3$;

Compounds of Formula [I] wherein $R^1$ is $-OH$ or $-OCH_3$, $R^2$ is $-C(O)H$, $R^3$ is $-CH_3$, $R^4$ and $R^5$ taken together, are $-(CH_2)_2-$, is $R^6$ is $-CH_3$, $R^7$ is $-H$, $R^8$ is $-H$, $R^9$ is $-CH_3$, and $R^{10}$ is $-CH_3$; and Compounds of Formula [I] wherein $R^1$ is $-OH$ or $-OCH_3$, $R^2$ is $-C(O)H$, $R^3$ is $-CH_3$, $R^4$ is $-H$, $R^5$ is $-CH_3$, $R^6$ and $R^7$, taken together, are $-(CH_2)_3-$, $R_8$ is $-H$, is $R_9$ is $-CH_3$, and $R_{10}$ is $-CH_3$.

Specific compounds of Formula [I] which are most preferred, for reasons of fragrance characteristics, synthesis advantages, formulation benefits, and/or other values are as follows:

The compound of Formula [I] wherein $R^1$ is $-OCH_3$, $R^2$ is $-C(O)H$, $R^3$ is $-CH_3$, $R^4$ is $-H$, $R^5$ is $-CH_3$, is $CH_3$, $R^7$ is $-CH_3$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-CH_2CH_3$, $R^4$ is $-H$, $R^5$ is $CH_3$, $R^6$ is $CH_3$, $R^7$ is $-CH_3$, $R^8$ is $-H$, $R^9$ is $-CH_3$, and $R^{10}$ is $-CH_3$;

The compound of Formula [I] wherein $R^1$ is $-OH$, $R^2$ is $-C(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$, and $R^{10}$ is $-CH_3$;

The compound of Formula [I] wherein $R^1$ is $-OH$, $R^2$ is $-C(O)H$, $R^3$ is $-CH_2CH_3$, $R^4$ is $-H$, $R^5$ is $CH_3$, $R^6$ is $CH_3$, and $R^7$ is $-CH_3$, $R^8$ is $-H$, $R^9$ is $-CH_3$, and $R^{10}$ is $-CH_3$;

The compound of Formula [I] wherein $R^1$ is $-OH$, $R^2$ is $-C(O)H$, $R^3$ is $-CH_3$, $R^4$ and $R^5$, taken together, are $-(CH_2)_2-$, $R^6$ is $-CH_3$, $R^7$ is $-H$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-CH_3$, $R^4$ and $R^5$, taken together, are $-(CH_2)_2-$, $R^6$ is $-CH_3$, $R^7$ is $-H$, $R^8$ is $-H$, $R^9$ is $-CH_3$, and $R^{10}$ is $-CH_3$;

The compound of Formula [I] wherein $R^1$ is $-OH$, $R^2$ is $-C(O)H$, $R^3$ is $-CH_3$, $R^4$ is $-H$, $R^5$ is $-CH_3$, $R^6$ and $R^7$, taken together, are $-(CH_2)_3-$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-CH_3$, $R^4$ is $-H$, $R^5$ is $-CH_3$, $R^6$ and $R^7$, taken together, are $(CH_2)_3-$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-CH_3$, $R^4$ is $-H$, $R^5$ is $-CH_3$, $R^6$ is $-CH_3$, $R^7$ is $-H$, $R^8$ is $-CH_3$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-OCH_3$, $R^4$ is $-H$, $R^5$ is $-CH_3$, $R^6$ is $-CH_3$, $R^7$ is $-H$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-OCH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$; and The compound of Formula [I] wherein $R^1$ is $-OCH_3$, $R^2$ is $-H$, $R^3$ is $-C(O)H$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Of the foregoing compounds, the most preferred compounds are as follows:

The compound of Formula [I] wherein $R^1$ is $-OCH_3$, $R^2$ is $-C(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-CH_3$, $R^4$ is $-H$, $R^5$ is $-CH_3$, $R^6$ is $-CH_3$, $R^7$ is $-H$, $R^8$ is $-CH_3$, $R^9$ is $-CH_3$, and $R^{10}$ is $-CH_3$;

The compound of Formula [I] wherein $R^1$ is $-OCH_3$, $R^2$ is $-C(O)H$, $R^3$ is $-OCH_3$, $R^4$ is $-H$, $R^5$ is $-CH_3$, $R^6$ is $-CH_3$, $R^7$ is $-H$, $R^8$ is $-H$, $R^9$ is $-CH_3$, and $R^{10}$ is $-CH_3$;

The compound of Formula [I] wherein $R^1$ is —OCH$_3$, $R^2$ is —C(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$; and The compound of Formula [I] wherein $R^1$ is —OCH$_3$, $R^2$ is —H, $R^3$ is —C(O)H, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$.

The novel alkyl tetralin aldehyde compounds of the present invention may be prepared in various fashions. In the preferable protocol, alkyl tetralins are first prepared. Then the alkyl tetralins are formylated (that is, the radical —C(O)H is added to the benzene ring of the tetralin structure, to form an alkyl tetralin aidehyde), or oxidized (that is, a —CH$_3$ substituent on the benzene ring of the tetralin structure is oxidized to —C(O)H, to form an alkyl tetralin aidehyde). Examples 1–4 illustrate specific methodology which may be utilized for the preparation of compounds of the present invention.

In general, alkyl tetralin compounds or alkyl tetralin aldehyde compounds may be prepared by numerous synthetic routes which will be readily apparent to those skilled in the art, once armed with the present disclosure. Examples of suitable methodology which may be employed or modified in accordance with the present disclosures to prepare compounds of the present invention include Frank, U.S. Pat. Nos. 4,877,911, 4,877,914, 4,877,910, 4,877,916, 4,877,915, 4,877,913, 4,877,912, and 5,087,785, Carpenter, U.S. Pat. Nos. 2,897,237, 2,800,511, Fehr et al., U.S. Pat. No. 5,162,588, Willis et al., U.S. Pat. No. 4,605,778, Traas et al., U.S. Pat. No. 4,352,748, Cobb et al., U.S. Pat. No. 4,551,573, Wood, U.S. Pat. No. 3,246,044, Wood et al., U.S. Pat. No. 3,856,875, Sato et al., U.S. Pat. No. 4,284,818, Kahn, U.S. Pat. No. 3,379,785, Suzukamo et al., U.S. Pat. No. 4,767,882, Gonzenbach, U.S. Pat. No. 4,908,349, European Patent Application Publication No. 0 393 742, European Patent Application Publication No. 0 301 375, Japanese Patent No. SHO 57-40420, Fehr et al., *Helv. Chim. Acta*, Vol. 72, pp. 1537–1553 (1989), and Bedoukian, Paul Z., *Perfumery and Flavoring Synthetics*, 3rd ed., pp. 334–336, Allured Publishing Corporation, Wheaton, Ill. (1986), the disclosures of each of which are hereby incorporated herein by reference, in their entirety.

In accordance with Frank, U.S. Pat. No. 4,877,910, for example, various polyalkyl tetrahydronapthalene compounds may be prepared by carrying out a cyclialkylation reaction between an olefinic compound and a substituted benzene compound in the presence of a hydride abstracting reagent, an alkyl halide or hydrogen halide, a Lewis acid, and, optionally, a phase transfer agent. Suitable olefinic compounds include 2,3-dimethyl-1-butene and 2,3-dimethyl-2-butene. Suitable substituted benzene compounds include isopropyl toluene (para-cymene), 1-ethyl-4-isopropylbenzene, 1-n-propyl-4-isopropyl-benzene, and 1-tertiary-butyl-4-isopropyl-benzene. A suitable hydride abstracting reagent is 2,4,4-trimethyl-2-pentene (diisobutylene-2). Suitable alkyl halides include tertiary-butyl chloride, tertiary-amyl chloride, 2-methyl-2-chloropentane, 3-methyl-3-chloropentane and 1,8-dichloro-para-menthane. Suitable Lewis acids include aluminum chloride, aluminum bromide, aluminum iodide, monofluorodichloroaluminum, monobromodichloroaluminum and monoiododichloroaluminum. Suitable phase transfer agents include methyltrioctylammonium chloride (referred to herein as "MTOAc"), and a mixture of methyltrioctyl-ammonium chloride and methyltridecylammonium chloride (the mixture being marketed under the tradename Adogen-464 TM, by Sherex Co., located in Dublin, Ohio).

In general, the molar proportions of the reagents employed in the foregoing process can be varied over a relatively wide range. However, where phase transfer agents are employed in the process, it is important, for the best results, to maintain a ratio of less than one mole of phase transfer agent per mole of Lewis acid. Preferably, the molar ratio is about 0.8 to 1.0, more preferably 0.5 to 1.0, phase transfer agent to Lewis acid. In addition, it is also preferable to use a mixture of olefinic compound, hydride abstracting reagent, alkyl halide and hydrogen halide, wherein these components are present in a molar range of about 1.0 to about 5.0 moles of olefin per mole of combined halides plus reagent. More preferably, the olefin, and the combined halides plus reagent are present in nearly equimolar amounts, that is, about 1.0 mole of olefin per mole of combined halides plus reagent. Preferably, the substituted benzene compound is present in a range of about 0.5 to about 10 moles per mole of olefin, more preferably in a range of about 0.5 to about 5.0 per mole of olefin. In a most preferred embodiment, each of the benzene compound, olefin, and the combination of alkyl halide, hydrogen halide plus hydride abstracting reagent, are present nearly in equimolar amounts, that is, about 1.0 mole of benzene compound, to about 1.0 mole of olefin, to about 1.0 mole of combined halides plus hydride abstracting reagent. The amount of Lewis acid utilized is preferably in the range of about 2% to about 10% by weight of the Lewis acid based on the combined weight of the substituted benzene, olefin, alkyl halide, hydrogen halide plus hydride abstracting reagent.

The foregoing reaction is generally carried out using a solvent, although, if desired, substituted benzene, one of the starting materials, may be employed in large excess in lieu of an additional solvent. Suitable solvents include methylene chloride, chloroform, carbon tetrachloride, ethylene chloride, ethylidene chloride, 1,1,1-trichloroethane, 1,1,2-trichloroethane, 1,1,2,2-tetrachloroethane, 1,2-dichloroethylene, trichloro-ethylene, tetrachloroethylene, 1,2,3-trichloropropane, amyl chloride, ethylene bromide, monochlorobenzene, ortho-dichlorobenzene, bromobenzene, fluorobenzene, n-hexane, n-heptane, n-octane, benzene, toluene, ethylbenzene and xylene. Preferred for reasons of yield, safety and/or process engineering are the unhalogenated aliphatic and unhalogenated alicyclic hydrocarbons.

The alkylation reaction described above can be carried out in any suitable vessel which provides efficient contacting between the Lewis acid and the other reactants. For simplicity, a stirred batch reactor can be employed. Moreover, the reaction vessel used should be resistant to the possibly corrosive nature of the catalyst. Glass-lined vessels would be suitable for this purpose. Additional vessel materials will be apparent to those skilled in the art.

The reagents of the present process may be added in any order, although where the process is carried out with a phase transfer agent, the preferred mode is to add the solvent, the Lewis acid and the phase transfer agent first, allow sufficient time for the Lewis acid to become substantially dissolved in the solvent, and then add the remaining reagents. Generally, 15 to 30 minutes are needed for the Lewis acid to become substantially dissolved in the solvent.

Ideally, the reaction is carried out at temperatures ranging from about −30° C. to about 50° C., preferably at temperatures ranging from about −10° C. to about 40° C., and most preferably at temperatures ranging from about 0° C. to about 30° C.

The pressure at which the reaction is carried out is not critical. If the reaction is carried out in a sealed vessel, autogenous pressure is acceptable, although higher or lower pressures, if desired, may be employed. The reaction can also be carried out at atmospheric pressure in an open reaction vessel, in which case the vessel is preferably equipped with a moisture trap to prevent significant exposure of Lewis acid to moisture. The reaction can take place in an oxygen atmosphere, or an inert atmosphere as in the presence of a gas such as nitrogen, argon and the like, the type of atmosphere also not being critical.

Reaction time is generally rather short and is often dictated by the kind of equipment employed. Sufficient time must be provided, however, for thorough contacting of the substituted benzene compound, the olefinic compound, the Lewis acid and the phase transfer agent. Generally the reaction proceeds to completion in about 1 to about 7 hours.

Product can be recovered by first quenching the reaction mixture in cold water or on crushed ice, preferably on ice, and then processing the mixture in the usual manner for Friedel-Crafts reactions to extract the desired alkyl-substituted tetrahydronaphthalene compounds. Suitable extraction protocol is described, for example, in *Friedel-Crafts Reactions.* Typically, following quenching and the resultant phase separation, the organic layer is washed an additional time with water to aid in removal of the Lewis acid. One or more additional washings can be carried out with dilute alkali solution to further aid Lewis acid removal. Pure product can then be recovered by subjecting the washed reaction mixture to reduced pressure fractional distillation.

Exemplary tetrahydronaphthalene compounds which may be prepared by the foregoing process include 1,1,3,4,4,6-hexamethyl-1,2,3,4-tetrahydronaphthalene (HMT), 6-ethyl-1,1,3,4,4-pentamethyl-1,2,3,4-tetrahydronaphthalene, 6-tertiary-butyl-1,1,3,4,4-pentamethyl-1,2,3,4-tetra-hydronaphthalene, and 6-n-propyl-1,1,3,4,4-pentamethyl-1,2,3,4-tetrahydronaphthalene.

The disclosures of Frank, U.S. Pat. No. 4,877,910, are hereby incorporated herein by reference in their entirety.

Alkyl tetralin compounds may then be formylated or oxidized to form alkyl tetralin aldehydes using conventional formylation or oxidation technology, as will be readily apparent to one skilled in the art once armed with the present disclosure.

Specifically, to prepare alkyl tetralin aldehydes from alkyl tetralins using formylation techniques, the alkyl tetralins are preferably reacted with $\alpha,\alpha$-dichloromethyl methyl ether, in a solvent such as an organic solvent (preferably a halogenated organic solvent such as, for example, anhydrous methylene chloride), in the presence of a Lewis acid (preferably titanium tetrachloride). Other suitable halogenated solvents and Lewis acids are described above, and will be readily apparent to those skilled in the art, once armed with the present disclosures. In general, formylation methods are well known in the art, and are described in many of the patents and publications discussed above for the preparation of alkyl tetralin compounds, as well as, for example, in *Organic Syntheses,* Collective Vol. 5, pp. 49–50, by A. Rieche, H. Gross, and E. Hoft, edited by H. E. Baumgarten, John Wiley and Sons (New York, N.Y. 1973), Rahm, *Synthetic Communications,* Vol. 12, No. 6, pp. 485–487 (1982), Effenberger, *Angewandte Chemie International Edition (English),* Vol. 19, No. 3, pp. 151–230 (1980), Olah et al., *Chemical Reviews,* Vol. 87, No. 4, pp. 671–686 (1987), and Hauser et al., *Synthesis,* pp. 723–724 (August 1987), the disclosures of each of which are incorporated herein by reference, in their entirety.

Alternatively, to prepare alkyl tetralin aldehydes from alkyl tetralins using oxidation techniques, the alkyl tetralins are preferably reacted with ceric ammonium nitrate ($Ce(NO_3)_4 \bullet NH_4NO_3$), a strong oxidant for organic compounds, in the presence of acetic acid. In general, these and other suitable oxidation methods are well known in the art, and are described, for example, in Syper, *Tetrahedron Letters,* No. 37, pp. 4493–4498 (1966), Laing et al., *J. Chem. Soc. (C),* pp. 2915–2918 (1968), Imamoto et al., *Chemistry Letters,* pp. 1445–1446 (1990), Kreh et al., *Tetrahedron Letters,* Vol. 28, No. 10, pp. 1067–1068 (1987), Hauser et al., *Communications,* pp. 72–73 (August 1987), and Syper, *Tetrahedron Letters,* No. 42, pp. 4193–4198 (1967).

Further purification of the alkyl tetralin aldehyde compounds of Formula [I] may be carried out, if desired, using, for example, standard fractional distillation techniques, as well as other conventional extraction, distillation, crystallization and chromatography techniques, and the like.

Exemplary novel alkyl tetralin aldehyde compounds are shown in Table I below.

TABLE I

| Compound | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 1 | —$CH_3$ | —$OCH_3$ | —$C(O)H$ | —H | —H | —$CH_3$ | —H | —H | —$CH_3$ | —$CH_3$ |
| 2 | —$CH_3$ | —$OCH_3$ | —$C(O)H$ | —H | —H | —$CH_3$ | —H | —H | —$CH_2CH_3$ | —$CH_3$ |
| 3 | —$CH_3$ | —$OCH_3$ | —$C(O)H$ | —H | —H | —$CH_2CH_3$ | —H | —H | —$CH_3$ | —$CH_3$ |
| 4 | —$CH_3$ | —$OCH_3$ | —$C(O)H$ | —H | —$CH_3$ | —$CH_3$ | —H | —H | —$CH_3$ | —$CH_3$ |
| 5 | —$CH_3$ | —$OCH_3$ | —$C(O)H$ | —H | —$CH_3$ | —$CH_3$ | —H | —H | —$CH_2CH_3$ | —$CH_3$ |
| 6 | —$CH_3$ | —$OCH_3$ | —$C(O)H$ | —H | —$CH_3$ | —$CH_2CH_3$ | —H | —H | —$CH_3$ | —$CH_3$ |
| 7 | —$CH_3$ | —$OCH_3$ | —$C(O)H$ | —H | —$CH_3$ | —$CH_2CH_3$ | —H | —H | —$CH_3$ | —$CH_3$ |
| 8 | —$CH_3$ | —$OCH_3$ | —$C(O)H$ | —H | —$CH_3$ | —$CH_3$ | —H | —H | —H | —$CH_3$ |
| 9 | —$CH_3$ | —$OCH_3$ | —$C(O)H$ | —H | —$CH_3$ | —$CH_2CH_3$ | —H | —H | —H | —$CH_3$ |
| 10 | —$CH_2CH_3$ | —$OCH_3$ | —$C(O)H$ | —H | —H | —$CH_3$ | —H | —H | —$CH_3$ | —$CH_3$ |
| 11 | —$CH_2CH_3$ | —$OCH_3$ | —$C(O)H$ | —H | —H | —$CH_3$ | —H | —H | —$CH_2CH_3$ | —$CH_3$ |
| 12 | —$CH_2CH_3$ | —$OCH_3$ | —$C(O)H$ | —H | —H | —$CH_2CH_3$ | —H | —H | —$CH_3$ | —$CH_3$ |
| 13 | —$CH_2CH_3$ | —$OCH_3$ | —$C(O)H$ | —H | —$CH_3$ | —$CH_3$ | —H | —H | —$CH_3$ | —$CH_3$ |
| 14 | —$CH_2CH_3$ | —$OCH_3$ | —$C(O)H$ | —H | —$CH_3$ | —$CH_3$ | —H | —H | —$CH_2CH_3$ | —$CH_3$ |
| 15 | —$CH_2CH_3$ | —$OCH_3$ | —$C(O)H$ | —H | —$CH_3$ | —$CH_2CH_3$ | —H | —H | —$CH_3$ | —$CH_3$ |
| 16 | —$CH_2CH_3$ | —$OCH_3$ | —$C(O)H$ | —H | —$CH_3$ | —$CH_2CH_3$ | —H | —H | —$CH_3$ | —$CH_3$ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 17 | —CH₂CH₃ | —OCH₃ | —C(O)H | —H | —CH₃ | —CH₃ | —H | —H | —H | —CH₃ |
| 18 | —CH₂CH₃ | —OCH₃ | —C(O)H | —H | —CH₃ | —CH₂CH₃ | —H | —H | —H | —CH₃ |
| 19 | —CH₃ | —OH | —C(O)H | —H | —H | —CH₃ | —H | —H | —CH₃ | —CH₃ |
| 20 | —CH₃ | —OH | —C(O)H | —H | —H | —CH₃ | —H | —H | —CH₂CH₃ | —CH₃ |
| 21 | —CH₃ | —OH | —C(O)H | —H | —H | —CH₂CH₃ | —H | —H | —CH₃ | —CH₃ |
| 22 | —CH₃ | —OH | —C(O)H | —H | —CH₃ | —CH₃ | —H | —H | —CH₃ | —CH₃ |
| 23 | —CH₃ | —OH | —C(O)H | —H | —CH₃ | —CH₃ | —H | —H | —CH₂CH₃ | —CH₃ |
| 24 | —CH₃ | —OH | —C(O)H | —H | —CH₃ | —CH₂CH₃ | —H | —H | —CH₃ | —CH₃ |
| 25 | —CH₃ | —OH | —C(O)H | —H | —CH₃ | —CH₂CH₃ | —H | —H | —CH₃ | —CH₃ |
| 26 | —CH₃ | —OH | —C(O)H | —H | —CH₃ | —CH₃ | —H | —H | —H | —CH₃ |
| 27 | —CH₃ | —OH | —C(O)H | —H | —CH₃ | —CH₂CH₃ | —H | —H | —H | —CH₃ |
| 28 | —CH₂CH₃ | —OH | —C(O)H | —H | —H | —CH₃ | —H | —H | —CH₃ | —CH₃ |
| 29 | —CH₂CH₃ | —OH | —C(O)H | —H | —H | —CH₃ | —H | —H | —CH₂CH₃ | —CH₃ |
| 30 | —CH₂CH₃ | —OH | —C(O)H | —H | —H | —CH₂CH₃ | —H | —H | —CH₃ | —CH₃ |
| 31 | —CH₂CH₃ | —OH | —C(O)H | —H | —CH₃ | —CH₃ | —H | —H | —CH₃ | —CH₃ |
| 32 | —CH₂CH₃ | —OH | —C(O)H | —H | —CH₃ | —CH₃ | —H | —H | —CH₂CH₃ | —CH₃ |
| 33 | —CH₂CH₃ | —OH | —C(O)H | —H | —CH₃ | —CH₂CH₃ | —H | —H | —CH₃ | —CH₃ |
| 34 | —CH₂CH₃ | —OH | —C(O)H | —H | —CH₃ | —CH₂CH₃ | —H | —H | —CH₃ | —CH₃ |
| 35 | —CH₂CH₃ | —OH | —C(O)H | —H | —CH₃ | —CH₃ | —H | —H | —H | —CH₃ |
| 36 | —CH₂CH₃ | —OH | —C(O)H | —H | —CH₃ | —CH₂CH₃ | —H | —H | —H | —CH₃ |
| 37 | —OCH₃ | —CH₃ | —C(O)H | —H | —H | —CH₃ | —H | —H | —CH₃ | —CH₃ |
| 38 | —OCH₃ | —CH₃ | —C(O)H | —H | —H | —CH₃ | —H | —H | —CH₂CH₃ | —CH₃ |
| 39 | —OCH₃ | —CH₃ | —C(O)H | —H | —H | —CH₃ | —H | —CH₃ | —CH₃ | —CH₃ |
| 40 | —OCH₃ | —CH₃ | —C(O)H | —H | —H | —CH₃ | —H | —CH₃ | —CH₂CH₃ | —CH₃ |
| 41 | —OCH₃ | —CH₃ | —C(O)H | —H | —H | —CH₃ | —H | —CH₂CH₃ | —CH₃ | —CH₃ |
| 42 | —OCH₃ | —CH₃ | —C(O)H | —H | —H | —CH₃ | —CH₃ | —H | —CH₃ | —CH₃ |
| 43 | —OCH₃ | —CH₃ | —C(O)H | —H | —H | —CH₃ | —CH₃ | —H | —CH₂CH₃ | —CH₃ |
| 44 | —OCH₃ | —CH₃ | —C(O)H | —H | —H | —CH₃ | —CH₃ | —CH₃ | —CH₃ | —CH₃ |
| 45 | —OCH₃ | —CH₃ | —C(O)H | —H | —H | —CH₃ | —CH₃ | —CH₃ | —CH₂CH₃ | —CH₃ |
| 46 | —OCH₃ | —CH₃ | —C(O)H | —H | —H | —CH₃ | —CH₃ | —CH₂CH₃ | —CH₃ | —CH₃ |
| 47 | —OCH₃ | —CH₃ | —C(O)H | —H | —H | —CH₃ | —CH₂CH₃ | —H | —CH₃ | —CH₃ |
| 48 | —OCH₃ | —CH₃ | —C(O)H | —H | —H | —CH₃ | —CH₂CH₃ | —CH₃ | —CH₃ | —CH₃ |
| 49 | —OCH₃ | —CH₃ | —C(O)H | —H | —H | —CH₂CH₃ | —H | —H | —CH₃ | —CH₃ |
| 50 | —OCH₃ | —CH₃ | —C(O)H | —H | —H | —CH₂CH₃ | —H | —CH₃ | —CH₃ | —CH₃ |
| 51 | —OCH₃ | —CH₃ | —C(O)H | —H | —H | —CH₂CH₃ | —CH₃ | —H | —CH₃ | —CH₃ |
| 52 | —OCH₃ | —CH₃ | —C(O)H | —H | —H | —CH₂CH₃ | —CH₃ | —CH₃ | —CH₃ | —CH₃ |
| 53 | —OCH₃ | —CH₃ | —C(O)H | —H | —CH₃ | —CH₃ | —H | —H | —CH₃ | —CH₃ |
| 54 | —OCH₃ | —CH₃ | —C(O)H | —H | —CH₃ | —CH₃ | —H | —H | —CH₂CH₃ | —CH₃ |
| 55 | —OCH₃ | —CH₃ | —C(O)H | —H | —CH₃ | —CH₃ | —H | —CH₃ | —CH₃ | —CH₃ |
| 56 | —OCH₃ | —CH₃ | —C(O)H | —H | —CH₃ | —CH₃ | —H | —CH₃ | —CH₂CH₃ | —CH₃ |
| 57 | —OCH₃ | —CH₃ | —C(O)H | —H | —CH₃ | —CH₃ | —H | —CH₂CH₃ | —CH₃ | —CH₃ |
| 58 | —OCH₃ | —CH₃ | —C(O)H | —H | —CH₃ | —CH₃ | —CH₃ | —H | —CH₃ | —CH₃ |
| 59 | —OCH₃ | —CH₃ | —C(O)H | —H | —CH₃ | —CH₃ | —CH₃ | —H | —CH₂CH₃ | —CH₃ |
| 60 | —OCH₃ | —CH₃ | —C(O)H | —H | —CH₃ | —CH₃ | —CH₃ | —CH₃ | —CH₃ | —CH₃ |
| 61 | —OCH₃ | —CH₃ | —C(O)H | —H | —CH₃ | —CH₃ | —CH₃ | —CH₃ | —CH₂CH₃ | —CH₃ |
| 62 | —OCH₃ | —CH₃ | —C(O)H | —H | —CH₃ | —CH₃ | —CH₃ | —CH₂CH₃ | —CH₃ | —CH₃ |
| 63 | —OCH₃ | —CH₃ | —C(O)H | —H | —CH₃ | —CH₃ | —CH₂CH₃ | —H | —CH₃ | —CH₃ |
| 64 | —OCH₃ | —CH₃ | —C(O)H | —H | —CH₃ | —CH₃ | —CH₂CH₃ | —CH₃ | —CH₃ | —CH₃ |
| 65 | —OCH₃ | —CH₃ | —C(O)H | —H | —CH₃ | —CH₂CH₃ | —H | —H | —CH₃ | —CH₃ |
| 66 | —OCH₃ | —CH₃ | —C(O)H | —H | —CH₃ | —CH₂CH₃ | —H | —CH₃ | —CH₃ | —CH₃ |
| 67 | —OCH₃ | —CH₃ | —C(O)H | —H | —CH₃ | —CH₂CH₃ | —CH₃ | —H | —CH₃ | —CH₃ |
| 68 | —OCH₃ | —CH₃ | —C(O)H | —H | —CH₃ | —CH₂CH₃ | —CH₃ | —CH₃ | —CH₃ | —CH₃ |
| 69 | —OCH₃ | —CH₃ | —C(O)H | —H | —CH₃ | —CH₂CH₃ | —H | —H | —CH₃ | —CH₃ |
| 70 | —OCH₃ | —CH₃ | —C(O)H | —H | —CH₃ | —CH₂CH₃ | —H | —CH₃ | —CH₃ | —CH₃ |
| 71 | —OCH₃ | —CH₃ | —C(O)H | —H | —CH₃ | —CH₂CH₃ | —CH₃ | —H | —CH₃ | —CH₃ |
| 72 | —OCH₃ | —CH₃ | —C(O)H | —H | —CH₃ | —CH₂CH₃ | —CH₃ | —CH₃ | —CH₃ | —CH₃ |
| 73 | —OCH₃ | —CH₃ | —C(O)H | —H | —CH₃ | —CH₃ | —H | —H | —H | —CH₃ |
| 74 | —OCH₃ | —CH₃ | —C(O)H | —H | —CH₃ | —CH₂CH₃ | —H | —H | —H | —CH₃ |
| 75 | —OCH₃ | —CH₃ | —C(O)H | —H | —CH₃ | —CH₃ | —H | —CH₃ | —H | —CH₃ |
| 76 | —OCH₃ | —CH₃ | —C(O)H | —H | —CH₃ | —CH₂CH₃ | —H | —CH₃ | —H | —CH₃ |
| 77 | —OCH₃ | —CH₃ | —C(O)H | —H | —CH₃ | —CH₃ | —H | —CH₂CH₃ | —H | —CH₃ |
| 78 | —OCH₃ | —CH₃ | —C(O)H | —H | —CH₃ | —CH₃ | —CH₃ | —H | —H | —CH₃ |
| 79 | —OCH₃ | —CH₃ | —C(O)H | —H | —CH₃ | —CH₂CH₃ | —CH₃ | —H | —H | —CH₃ |
| 80 | —OCH₃ | —CH₃ | —C(O)H | —H | —CH₃ | —CH₃ | —CH₃ | —CH₃ | —H | —CH₃ |
| 81 | —OCH₃ | —CH₃ | —C(O)H | —H | —CH₃ | —CH₂CH₃ | —CH₃ | —CH₃ | —H | —CH₃ |
| 82 | —OCH₃ | —CH₃ | —C(O)H | —H | —CH₃ | —CH₃ | —CH₃ | —CH₂CH₃ | —H | —CH₃ |
| 83 | —OCH₃ | —CH₃ | —C(O)H | —H | —CH₃ | —CH₃ | —CH₂CH₃ | —H | —H | —CH₃ |
| 84 | —OCH₃ | —CH₃ | —C(O)H | —H | —CH₃ | —CH₃ | —CH₂CH₃ | —CH₃ | —H | —CH₃ |
| 85 | —OCH₃ | —CH₂CH₃ | —C(O)H | —H | —H | —CH₃ | —H | —H | —CH₃ | —CH₃ |
| 86 | —OCH₃ | —CH₂CH₃ | —C(O)H | —H | —H | —CH₃ | —H | —H | —CH₂CH₃ | —CH₃ |
| 87 | —OCH₃ | —CH₂CH₃ | —C(O)H | —H | —H | —CH₃ | —H | —CH₃ | —CH₃ | —CH₃ |
| 88 | —OCH₃ | —CH₂CH₃ | —C(O)H | —H | —H | —CH₃ | —H | —CH₃ | —CH₂CH₃ | —CH₃ |
| 89 | —OCH₃ | —CH₂CH₃ | —C(O)H | —H | —H | —CH₃ | —H | —CH₂CH₃ | —CH₃ | —CH₃ |
| 90 | —OCH₃ | —CH₂CH₃ | —C(O)H | —H | —H | —CH₃ | —CH₃ | —H | —CH₃ | —CH₃ |
| 91 | —OCH₃ | —CH₂CH₃ | —C(O)H | —H | —H | —CH₃ | —CH₃ | —H | —CH₂CH₃ | —CH₃ |
| 92 | —OCH₃ | —CH₂CH₃ | —C(O)H | —H | —H | —CH₃ | —CH₃ | —CH₃ | —CH₃ | —CH₃ |
| 93 | —OCH₃ | —CH₂CH₃ | —C(O)H | —H | —H | —CH₃ | —CH₃ | —CH₃ | —CH₂CH₃ | —CH₃ |
| 94 | —OCH₃ | —CH₂CH₃ | —C(O)H | —H | —H | —CH₃ | —CH₃ | —CH₂CH₃ | —CH₃ | —CH₃ |
| 95 | —OCH₃ | —CH₂CH₃ | —C(O)H | —H | —H | —CH₃ | —CH₂CH₃ | —H | —CH₃ | —CH₃ |
| 96 | —OCH₃ | —CH₂CH₃ | —C(O)H | —H | —H | —CH₃ | —CH₂CH₃ | —CH₃ | —CH₃ | —CH₃ |
| 97 | —OCH₃ | —CH₂CH₃ | —C(O)H | —H | —H | —CH₂CH₃ | —H | —H | —CH₃ | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 98 | —OCH₃ | —CH₂CH₃ | —C(O)H | —H | —H | —CH₂CH₃ | —H | —CH₃ | —CH₃ | —CH₃ |
| 99 | —OCH₃ | —CH₂CH₃ | —C(O)H | —H | —H | —CH₂CH₃ | —CH₃ | —H | —CH₃ | —CH₃ |
| 100 | —OCH₃ | —CH₂CH₃ | —C(O)H | —H | —H | —CH₂CH₃ | —CH₃ | —CH₃ | —CH₃ | —CH₃ |
| 101 | —OCH₃ | —CH₂CH₃ | —C(O)H | —H | —CH₃ | —CH₃ | —H | —H | —CH₃ | —CH₃ |
| 102 | —OCH₃ | —CH₂CH₃ | —C(O)H | —H | —CH₃ | —CH₃ | —H | —H | —CH₂CH₃ | —CH₃ |
| 103 | —OCH₃ | —CH₂CH₃ | —C(O)H | —H | —CH₃ | —CH₃ | —H | —CH₃ | —CH₃ | —CH₃ |
| 104 | —OCH₃ | —CH₂CH₃ | —C(O)H | —H | —CH₃ | —CH₃ | —H | —CH₃ | —CH₂CH₃ | —CH₃ |
| 105 | —OCH₃ | —CH₂CH₃ | —C(O)H | —H | —CH₃ | —CH₃ | —H | —CH₂CH₃ | —CH₃ | —CH₃ |
| 106 | —OCH₃ | —CH₂CH₃ | —C(O)H | —H | —CH₃ | —CH₃ | —CH₃ | —H | —CH₃ | —CH₃ |
| 107 | —OCH₃ | —CH₂CH₃ | —C(O)H | —H | —CH₃ | —CH₃ | —CH₃ | —H | —CH₂CH₃ | —CH₃ |
| 108 | —OCH₃ | —CH₂CH₃ | —C(O)H | —H | —CH₃ | —CH₃ | —CH₃ | —CH₃ | —CH₃ | —CH₃ |
| 109 | —OCH₃ | —CH₂CH₃ | —C(O)H | —H | —CH₃ | —CH₃ | —CH₃ | —CH₃ | —CH₂CH₃ | —CH₃ |
| 110 | —OCH₃ | —CH₂CH₃ | —C(O)H | —H | —CH₃ | —CH₃ | —CH₃ | —CH₂CH₃ | —CH₃ | —CH₃ |
| 111 | —OCH₃ | —CH₂CH₃ | —C(O)H | —H | —CH₃ | —CH₃ | —CH₂CH₃ | —H | —CH₃ | —CH₃ |
| 112 | —OCH₃ | —CH₂CH₃ | —C(O)H | —H | —CH₃ | —CH₃ | —CH₂CH₃ | —CH₃ | —CH₃ | —CH₃ |
| 113 | —OCH₃ | —CH₂CH₃ | —C(O)H | —H | —CH₃ | —CH₂CH₃ | —H | —H | —CH₃ | —CH₃ |
| 114 | —OCH₃ | —CH₂CH₃ | —C(O)H | —H | —CH₃ | —CH₂CH₃ | —H | —CH₃ | —CH₃ | —CH₃ |
| 115 | —OCH₃ | —CH₂CH₃ | —C(O)H | —H | —CH₃ | —CH₂CH₃ | —CH₃ | —H | —CH₃ | —CH₃ |
| 116 | —OCH₃ | —CH₂CH₃ | —C(O)H | —H | —CH₃ | —CH₂CH₃ | —CH₃ | —CH₃ | —CH₃ | —CH₃ |
| 117 | —OCH₃ | —CH₂CH₃ | —C(O)H | —H | —CH₃ | —CH₂CH₃ | —H | —H | —CH₃ | —CH₃ |
| 118 | —OCH₃ | —CH₂CH₃ | —C(O)H | —H | —CH₃ | —CH₂CH₃ | —H | —CH₃ | —CH₃ | —CH₃ |
| 119 | —OCH₃ | —CH₂CH₃ | —C(O)H | —H | —CH₃ | —CH₂CH₃ | —CH₃ | —H | —CH₃ | —CH₃ |
| 120 | —OCH₃ | —CH₂CH₃ | —C(O)H | —H | —CH₃ | —CH₂CH₃ | —CH₃ | —CH₃ | —CH₃ | —CH₃ |
| 121 | —OCH₃ | —CH₂CH₃ | —C(O)H | —H | —CH₃ | —CH₃ | —H | —H | —H | —CH₃ |
| 122 | —OCH₃ | —CH₂CH₃ | —C(O)H | —H | —CH₃ | —CH₂CH₃ | —H | —H | —H | —CH₃ |
| 123 | —OCH₃ | —CH₂CH₃ | —C(O)H | —H | —CH₃ | —CH₃ | —H | —CH₃ | —H | —CH₃ |
| 124 | —OCH₃ | —CH₂CH₃ | —C(O)H | —H | —CH₃ | —CH₂CH₃ | —H | —CH₃ | —H | —CH₃ |
| 125 | —OCH₃ | —CH₂CH₃ | —C(O)H | —H | —CH₃ | —CH₃ | —H | —CH₂CH₃ | —H | —CH₃ |
| 126 | —OCH₃ | —CH₂CH₃ | —C(O)H | —H | —CH₃ | —CH₃ | —CH₃ | —H | —H | —CH₃ |
| 127 | —OCH₃ | —CH₂CH₃ | —C(O)H | —H | —CH₃ | —CH₂CH₃ | —CH₃ | —H | —H | —CH₃ |
| 128 | —OCH₃ | —CH₂CH₃ | —C(O)H | —H | —CH₃ | —CH₃ | —CH₃ | —CH₃ | —H | —CH₃ |
| 129 | —OCH₃ | —CH₂CH₃ | —C(O)H | —H | —CH₃ | —CH₂CH₃ | —CH₃ | —CH₃ | —H | —CH₃ |
| 130 | —OCH₃ | —CH₂CH₃ | —C(O)H | —H | —CH₃ | —CH₃ | —CH₃ | —CH₂CH₃ | —H | —CH₃ |
| 131 | —OCH₃ | —CH₂CH₃ | —C(O)H | —H | —CH₃ | —CH₃ | —CH₂CH₃ | —H | —H | —CH₃ |
| 132 | —OCH₃ | —CH₂CH₃ | —C(O)H | —H | —CH₃ | —CH₃ | —CH₂CH₃ | —CH₃ | —H | —CH₃ |
| 133 | —OCH₃ | —OCH₃ | —C(O)H | —H | —H | —CH₃ | —H | —H | —CH₃ | —CH₃ |
| 134 | —OCH₃ | —OCH₃ | —C(O)H | —H | —H | —CH₃ | —H | —H | —CH₂CH₃ | —CH₃ |
| 135 | —OCH₃ | —OCH₃ | —C(O)H | —H | —H | —CH₃ | —H | —CH₃ | —CH₃ | —CH₃ |
| 136 | —OCH₃ | —OCH₃ | —C(O)H | —H | —H | —CH₃ | —H | —CH₃ | —CH₂CH₃ | —CH₃ |
| 137 | —OCH₃ | —OCH₃ | —C(O)H | —H | —H | —CH₃ | —H | —CH₂CH₃ | —CH₃ | —CH₃ |
| 138 | —OCH₃ | —OCH₃ | —C(O)H | —H | —H | —CH₃ | —CH₃ | —H | —CH₃ | —CH₃ |
| 139 | —OCH₃ | —OCH₃ | —C(O)H | —H | —H | —CH₃ | —CH₃ | —H | —CH₂CH₃ | —CH₃ |
| 140 | —OCH₃ | —OCH₃ | —C(O)H | —H | —H | —CH₃ | —CH₃ | —CH₃ | —CH₃ | —CH₃ |
| 141 | —OCH₃ | —OCH₃ | —C(O)H | —H | —H | —CH₃ | —CH₃ | —CH₃ | —CH₂CH₃ | —CH₃ |
| 142 | —OCH₃ | —OCH₃ | —C(O)H | —H | —H | —CH₃ | —CH₃ | —CH₂CH₃ | —CH₃ | —CH₃ |
| 143 | —OCH₃ | —OCH₃ | —C(O)H | —H | —H | —CH₃ | —CH₂CH₃ | —H | —CH₃ | —CH₃ |
| 144 | —OCH₃ | —OCH₃ | —C(O)H | —H | —H | —CH₃ | —CH₂CH₃ | —CH₃ | —CH₃ | —CH₃ |
| 145 | —OCH₃ | —OCH₃ | —C(O)H | —H | —H | —CH₂CH₃ | —H | —H | —CH₃ | —CH₃ |
| 146 | —OCH₃ | —OCH₃ | —C(O)H | —H | —H | —CH₂CH₃ | —H | —CH₃ | —CH₃ | —CH₃ |
| 147 | —OCH₃ | —OCH₃ | —C(O)H | —H | —H | —CH₂CH₃ | —CH₃ | —H | —CH₃ | —CH₃ |
| 148 | —OCH₃ | —OCH₃ | —C(O)H | —H | —H | —CH₂CH₃ | —CH₃ | —CH₃ | —CH₃ | —CH₃ |
| 149 | —OCH₃ | —OCH₃ | —C(O)H | —H | —CH₃ | —CH₃ | —H | —H | —CH₃ | —CH₃ |
| 150 | —OCH₃ | —OCH₃ | —C(O)H | —H | —CH₃ | —CH₃ | —H | —H | —CH₂CH₃ | —CH₃ |
| 151 | —OCH₃ | —OCH₃ | —C(O)H | —H | —CH₃ | —CH₃ | —H | —CH₃ | —CH₃ | —CH₃ |
| 152 | —OCH₃ | —OCH₃ | —C(O)H | —H | —CH₃ | —CH₃ | —H | —CH₃ | —CH₂CH₃ | —CH₃ |
| 153 | —OCH₃ | —OCH₃ | —C(O)H | —H | —CH₃ | —CH₃ | —H | —CH₂CH₃ | —CH₃ | —CH₃ |
| 154 | —OCH₃ | —OCH₃ | —C(O)H | —H | —CH₃ | —CH₃ | —H | —CH₃ | —CH₃ | —CH₃ |
| 155 | —OCH₃ | —OCH₃ | —C(O)H | —H | —CH₃ | —CH₃ | —CH₃ | —H | —CH₂CH₃ | —CH₃ |
| 156 | —OCH₃ | —OCH₃ | —C(O)H | —H | —CH₃ | —CH₃ | —CH₃ | —CH₃ | —CH₃ | —CH₃ |
| 157 | —OCH₃ | —OCH₃ | —C(O)H | —H | —CH₃ | —CH₃ | —CH₃ | —CH₃ | —CH₂CH₃ | —CH₃ |
| 158 | —OCH₃ | —OCH₃ | —C(O)H | —H | —CH₃ | —CH₃ | —CH₃ | —CH₂CH₃ | —CH₃ | —CH₃ |
| 159 | —OCH₃ | —OCH₃ | —C(O)H | —H | —CH₃ | —CH₃ | —CH₂CH₃ | —H | —CH₃ | —CH₃ |
| 160 | —OCH₃ | —OCH₃ | —C(O)H | —H | —CH₃ | —CH₃ | —CH₂CH₃ | —CH₃ | —CH₃ | —CH₃ |
| 161 | —OCH₃ | —OCH₃ | —C(O)H | —H | —CH₃ | —CH₂CH₃ | —H | —H | —CH₃ | —CH₃ |
| 162 | —OCH₃ | —OCH₃ | —C(O)H | —H | —CH₃ | —CH₂CH₃ | —H | —CH₃ | —CH₃ | —CH₃ |
| 163 | —OCH₃ | —OCH₃ | —C(O)H | —H | —CH₃ | —CH₂CH₃ | —CH₃ | —H | —CH₃ | —CH₃ |
| 164 | —OCH₃ | —OCH₃ | —C(O)H | —H | —CH₃ | —CH₂CH₃ | —CH₃ | —CH₃ | —CH₃ | —CH₃ |
| 165 | —OCH₃ | —OCH₃ | —C(O)H | —H | —CH₃ | —CH₂CH₃ | —H | —H | —CH₃ | —CH₃ |
| 166 | —OCH₃ | —OCH₃ | —C(O)H | —H | —CH₃ | —CH₂CH₃ | —H | —CH₃ | —CH₃ | —CH₃ |
| 167 | —OCH₃ | —OCH₃ | —C(O)H | —H | —CH₃ | —CH₂CH₃ | —CH₃ | —H | —CH₃ | —CH₃ |
| 168 | —OCH₃ | —OCH₃ | —C(O)H | —H | —CH₃ | —CH₂CH₃ | —CH₃ | —CH₃ | —CH₃ | —CH₃ |
| 169 | —OCH₃ | —OCH₃ | —C(O)H | —H | —CH₃ | —CH₃ | —H | —H | —H | —CH₃ |
| 170 | —OCH₃ | —OCH₃ | —C(O)H | —H | —CH₃ | —CH₂CH₃ | —H | —H | —H | —CH₃ |
| 171 | —OCH₃ | —OCH₃ | —C(O)H | —H | —CH₃ | —CH₃ | —H | —CH₃ | —H | —CH₃ |
| 172 | —OCH₃ | —OCH₃ | —C(O)H | —H | —CH₃ | —CH₂CH₃ | —H | —CH₃ | —H | —CH₃ |
| 173 | —OCH₃ | —OCH₃ | —C(O)H | —H | —CH₃ | —CH₃ | —H | —CH₂CH₃ | —H | —CH₃ |
| 174 | —OCH₃ | —OCH₃ | —C(O)H | —H | —CH₃ | —CH₃ | —CH₃ | —H | —H | —CH₃ |
| 175 | —OCH₃ | —OCH₃ | —C(O)H | —H | —CH₃ | —CH₂CH₃ | —CH₃ | —H | —H | —CH₃ |
| 176 | —OCH₃ | —OCH₃ | —C(O)H | —H | —CH₃ | —CH₃ | —CH₃ | —CH₃ | —H | —CH₃ |
| 177 | —OCH₃ | —OCH₃ | —C(O)H | —H | —CH₃ | —CH₂CH₃ | —CH₃ | —CH₃ | —H | —CH₃ |
| 178 | —OCH₃ | —OCH₃ | —C(O)H | —H | —CH₃ | —CH₃ | —CH₃ | —CH₂CH₃ | —H | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 179 | —OCH₃ | —OCH₃ | —C(O)H | —H | —CH₃ | —CH₃ | —CH₂CH₃ | —H | —H | —CH₃ |
| 180 | —OCH₃ | —OCH₃ | —C(O)H | —H | —CH₃ | —CH₃ | —CH₂CH₃ | —CH₃ | —H | —CH₃ |
| 181 | —OH | —CH₃ | —C(O)H | —H | —H | —CH₃ | —H | —H | —CH₃ | —CH₃ |
| 182 | —OH | —CH₃ | —C(O)H | —H | —H | —CH₃ | —H | —H | —CH₂CH₃ | —CH₃ |
| 183 | —OH | —CH₃ | —C(O)H | —H | —H | —CH₃ | —H | —CH₃ | —CH₃ | —CH₃ |
| 184 | —OH | —CH₃ | —C(O)H | —H | —H | —CH₃ | —H | —CH₃ | —CH₂CH₃ | —CH₃ |
| 185 | —OH | —CH₃ | —C(O)H | —H | —H | —CH₃ | —H | —CH₂CH₃ | —CH₃ | —CH₃ |
| 186 | —OH | —CH₃ | —C(O)H | —H | —H | —CH₃ | —CH₃ | —H | —CH₃ | —CH₃ |
| 187 | —OH | —CH₃ | —C(O)H | —H | —H | —CH₃ | —CH₃ | —H | —CH₂CH₃ | —CH₃ |
| 188 | —OH | —CH₃ | —C(O)H | —H | —H | —CH₃ | —CH₃ | —CH₃ | —CH₃ | —CH₃ |
| 189 | —OH | —CH₃ | —C(O)H | —H | —H | —CH₃ | —CH₃ | —CH₃ | —CH₂CH₃ | —CH₃ |
| 190 | —OH | —CH₃ | —C(O)H | —H | —H | —CH₃ | —CH₃ | —CH₂CH₃ | —CH₃ | —CH₃ |
| 191 | —OH | —CH₃ | —C(O)H | —H | —H | —CH₃ | —CH₂CH₃ | —H | —CH₃ | —CH₃ |
| 192 | —OH | —CH₃ | —C(O)H | —H | —H | —CH₃ | —CH₂CH₃ | —CH₃ | —CH₃ | —CH₃ |
| 193 | —OH | —CH₃ | —C(O)H | —H | —H | —CH₂CH₃ | —H | —H | —CH₃ | —CH₃ |
| 194 | —OH | —CH₃ | —C(O)H | —H | —H | —CH₂CH₃ | —H | —CH₃ | —CH₃ | —CH₃ |
| 195 | —OH | —CH₃ | —C(O)H | —H | —H | —CH₂CH₃ | —CH₃ | —H | —CH₃ | —CH₃ |
| 196 | —OH | —CH₃ | —C(O)H | —H | —H | —CH₂CH₃ | —CH₃ | —CH₃ | —CH₃ | —CH₃ |
| 197 | —OH | —CH₃ | —C(O)H | —H | —CH₃ | —CH₃ | —H | —H | —CH₃ | —CH₃ |
| 198 | —OH | —CH₃ | —C(O)H | —H | —CH₃ | —CH₃ | —H | —H | —CH₂CH₃ | —CH₃ |
| 199 | —OH | —CH₃ | —C(O)H | —H | —CH₃ | —CH₃ | —H | —CH₃ | —CH₃ | —CH₃ |
| 200 | —OH | —CH₃ | —C(O)H | —H | —CH₃ | —CH₃ | —H | —CH₃ | —CH₂CH₃ | —CH₃ |
| 201 | —OH | —CH₃ | —C(O)H | —H | —CH₃ | —CH₃ | —H | —CH₂CH₃ | —CH₃ | —CH₃ |
| 202 | —OH | —CH₃ | —C(O)H | —H | —CH₃ | —CH₃ | —CH₃ | —H | —CH₃ | —CH₃ |
| 203 | —OH | —CH₃ | —C(O)H | —H | —CH₃ | —CH₃ | —CH₃ | —H | —CH₂CH₃ | —CH₃ |
| 204 | —OH | —CH₃ | —C(O)H | —H | —CH₃ | —CH₃ | —CH₃ | —CH₃ | —CH₃ | —CH₃ |
| 205 | —OH | —CH₃ | —C(O)H | —H | —CH₃ | —CH₃ | —CH₃ | —CH₃ | —CH₂CH₃ | —CH₃ |
| 206 | —OH | —CH₃ | —C(O)H | —H | —CH₃ | —CH₃ | —CH₃ | —CH₂CH₃ | —CH₃ | —CH₃ |
| 207 | —OH | —CH₃ | —C(O)H | —H | —CH₃ | —CH₃ | —CH₂CH₃ | —H | —CH₃ | —CH₃ |
| 208 | —OH | —CH₃ | —C(O)H | —H | —CH₃ | —CH₃ | —CH₂CH₃ | —CH₃ | —CH₃ | —CH₃ |
| 209 | —OH | —CH₃ | —C(O)H | —H | —CH₃ | —CH₂CH₃ | —H | —H | —CH₃ | —CH₃ |
| 210 | —OH | —CH₃ | —C(O)H | —H | —CH₃ | —CH₂CH₃ | —H | —CH₃ | —CH₃ | —CH₃ |
| 211 | —OH | —CH₃ | —C(O)H | —H | —CH₃ | —CH₂CH₃ | —CH₃ | —H | —CH₃ | —CH₃ |
| 212 | —OH | —CH₃ | —C(O)H | —H | —CH₃ | —CH₂CH₃ | —CH₃ | —CH₃ | —CH₃ | —CH₃ |
| 213 | —OH | —CH₃ | —C(O)H | —H | —CH₃ | —CH₂CH₃ | —CH₃ | —H | —CH₃ | —CH₃ |
| 214 | —OH | —CH₃ | —C(O)H | —H | —CH₃ | —CH₂CH₃ | —H | —CH₃ | —CH₃ | —CH₃ |
| 215 | —OH | —CH₃ | —C(O)H | —H | —CH₃ | —CH₂CH₃ | —CH₃ | —H | —CH₃ | —CH₃ |
| 216 | —OH | —CH₃ | —C(O)H | —H | —CH₃ | —CH₂CH₃ | —CH₃ | —CH₃ | —CH₃ | —CH₃ |
| 217 | —OH | —CH₃ | —C(O)H | —H | —CH₃ | —CH₃ | —H | —H | —H | —CH₃ |
| 218 | —OH | —CH₃ | —C(O)H | —H | —CH₃ | —CH₂CH₃ | —H | —H | —H | —CH₃ |
| 219 | —OH | —CH₃ | —C(O)H | —H | —CH₃ | —CH₃ | —H | —CH₃ | —H | —CH₃ |
| 220 | —OH | —CH₃ | —C(O)H | —H | —CH₃ | —CH₂CH₃ | —H | —CH₃ | —H | —CH₃ |
| 221 | —OH | —CH₃ | —C(O)H | —H | —CH₃ | —CH₃ | —H | —CH₂CH₃ | —H | —CH₃ |
| 222 | —OH | —CH₃ | —C(O)H | —H | —CH₃ | —CH₃ | —CH₃ | —H | —H | —CH₃ |
| 223 | —OH | —CH₃ | —C(O)H | —H | —CH₃ | —CH₂CH₃ | —CH₃ | —H | —H | —CH₃ |
| 224 | —OH | —CH₃ | —C(O)H | —H | —CH₃ | —CH₃ | —CH₃ | —CH₃ | —H | —CH₃ |
| 225 | —OH | —CH₃ | —C(O)H | —H | —CH₃ | —CH₂CH₃ | —CH₃ | —CH₃ | —H | —CH₃ |
| 226 | —OH | —CH₃ | —C(O)H | —H | —CH₃ | —CH₃ | —CH₃ | —CH₂CH₃ | —H | —CH₃ |
| 227 | —OH | —CH₃ | —C(O)H | —H | —CH₃ | —CH₃ | —CH₂CH₃ | —H | —H | —CH₃ |
| 228 | —OH | —CH₃ | —C(O)H | —H | —CH₃ | —CH₃ | —CH₂CH₃ | —CH₃ | —H | —CH₃ |
| 229 | —OH | —CH₂CH₃ | —C(O)H | —H | —H | —CH₃ | —H | —H | —CH₃ | —CH₃ |
| 230 | —OH | —CH₂CH₃ | —C(O)H | —H | —H | —CH₃ | —H | —H | —CH₂CH₃ | —CH₃ |
| 231 | —OH | —CH₂CH₃ | —C(O)H | —H | —H | —CH₃ | —H | —CH₃ | —CH₃ | —CH₃ |
| 232 | —OH | —CH₂CH₃ | —C(O)H | —H | —H | —CH₃ | —H | —CH₃ | —CH₂CH₃ | —CH₃ |
| 233 | —OH | —CH₂CH₃ | —C(O)H | —H | —H | —CH₃ | —H | —CH₂CH₃ | —CH₃ | —CH₃ |
| 234 | —OH | —CH₂CH₃ | —C(O)H | —H | —H | —CH₃ | —CH₃ | —H | —CH₃ | —CH₃ |
| 235 | —OH | —CH₂CH₃ | —C(O)H | —H | —H | —CH₃ | —CH₃ | —H | —CH₂CH₃ | —CH₃ |
| 236 | —OH | —CH₂CH₃ | —C(O)H | —H | —H | —CH₃ | —CH₃ | —CH₃ | —CH₃ | —CH₃ |
| 237 | —OH | —CH₂CH₃ | —C(O)H | —H | —H | —CH₃ | —CH₃ | —CH₃ | —CH₂CH₃ | —CH₃ |
| 238 | —OH | —CH₂CH₃ | —C(O)H | —H | —H | —CH₃ | —CH₃ | —CH₂CH₃ | —CH₃ | —CH₃ |
| 239 | —OH | —CH₂CH₃ | —C(O)H | —H | —H | —CH₃ | —CH₂CH₃ | —H | —CH₃ | —CH₃ |
| 240 | —OH | —CH₂CH₃ | —C(O)H | —H | —H | —CH₃ | —CH₂CH₃ | —CH₃ | —CH₃ | —CH₃ |
| 241 | —OH | —CH₂CH₃ | —C(O)H | —H | —H | —CH₂CH₃ | —H | —H | —CH₃ | —CH₃ |
| 242 | —OH | —CH₂CH₃ | —C(O)H | —H | —H | —CH₂CH₃ | —H | —CH₃ | —CH₃ | —CH₃ |
| 243 | —OH | —CH₂CH₃ | —C(O)H | —H | —H | —CH₂CH₃ | —CH₃ | —H | —CH₃ | —CH₃ |
| 244 | —OH | —CH₂CH₃ | —C(O)H | —H | —H | —CH₂CH₃ | —CH₃ | —CH₃ | —CH₃ | —CH₃ |
| 245 | —OH | —CH₂CH₃ | —C(O)H | —H | —CH₃ | —CH₃ | —H | —H | —CH₃ | —CH₃ |
| 246 | —OH | —CH₂CH₃ | —C(O)H | —H | —CH₃ | —CH₃ | —H | —H | —CH₂CH₃ | —CH₃ |
| 247 | —OH | —CH₂CH₃ | —C(O)H | —H | —CH₃ | —CH₃ | —H | —CH₃ | —CH₃ | —CH₃ |
| 248 | —OH | —CH₂CH₃ | —C(O)H | —H | —CH₃ | —CH₃ | —H | —CH₃ | —CH₂CH₃ | —CH₃ |
| 249 | —OH | —CH₂CH₃ | —C(O)H | —H | —CH₃ | —CH₃ | —H | —CH₂CH₃ | —CH₃ | —CH₃ |
| 250 | —OH | —CH₂CH₃ | —C(O)H | —H | —CH₃ | —CH₃ | —CH₃ | —H | —CH₃ | —CH₃ |
| 251 | —OH | —CH₂CH₃ | —C(O)H | —H | —CH₃ | —CH₃ | —CH₃ | —H | —CH₂CH₃ | —CH₃ |
| 252 | —OH | —CH₂CH₃ | —C(O)H | —H | —CH₃ | —CH₃ | —CH₃ | —CH₃ | —CH₃ | —CH₃ |
| 253 | —OH | —CH₂CH₃ | —C(O)H | —H | —CH₃ | —CH₃ | —CH₃ | —CH₃ | —CH₂CH₃ | —CH₃ |
| 254 | —OH | —CH₂CH₃ | —C(O)H | —H | —CH₃ | —CH₃ | —CH₃ | —CH₂CH₃ | —CH₃ | —CH₃ |
| 255 | —OH | —CH₂CH₃ | —C(O)H | —H | —CH₃ | —CH₃ | —CH₂CH₃ | —H | —CH₃ | —CH₃ |
| 256 | —OH | —CH₂CH₃ | —C(O)H | —H | —CH₃ | —CH₃ | —CH₂CH₃ | —CH₃ | —CH₃ | —CH₃ |
| 257 | —OH | —CH₂CH₃ | —C(O)H | —H | —CH₃ | —CH₂CH₃ | —H | —H | —CH₃ | —CH₃ |
| 258 | —OH | —CH₂CH₃ | —C(O)H | —H | —CH₃ | —CH₂CH₃ | —H | —CH₃ | —CH₃ | —CH₃ |
| 259 | —OH | —CH₂CH₃ | —C(O)H | —H | —CH₃ | —CH₂CH₃ | —CH₃ | —H | —CH₃ | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 260 | —OH | —CH₂CH₃ | —C(O)H | —H | —CH₃ | —CH₂CH₃ | —CH₃ | —CH₃ | —CH₃ | —CH₃ |
| 261 | —OH | —CH₂CH₃ | —C(O)H | —H | —CH₃ | —CH₂CH₃ | —H | —H | —CH₃ | —CH₃ |
| 262 | —OH | —CH₂CH₃ | —C(O)H | —H | —CH₃ | —CH₂CH₃ | —H | —CH₃ | —CH₃ | —CH₃ |
| 263 | —OH | —CH₂CH₃ | —C(O)H | —H | —CH₃ | —CH₂CH₃ | —CH₃ | —H | —CH₃ | —CH₃ |
| 264 | —OH | —CH₂CH₃ | —C(O)H | —H | —CH₃ | —CH₂CH₃ | —CH₃ | —CH₃ | —CH₃ | —CH₃ |
| 265 | —OH | —CH₂CH₃ | —C(O)H | —H | —CH₃ | —CH₃ | —H | —H | —H | —CH₃ |
| 266 | —OH | —CH₂CH₃ | —C(O)H | —H | —CH₃ | —CH₂CH₃ | —H | —H | —H | —CH₃ |
| 267 | —OH | —CH₂CH₃ | —C(O)H | —H | —CH₃ | —CH₃ | —H | —CH₃ | —H | —CH₃ |
| 268 | —OH | —CH₂CH₃ | —C(O)H | —H | —CH₃ | —CH₂CH₃ | —H | —CH₃ | —H | —CH₃ |
| 269 | —OH | —CH₂CH₃ | —C(O)H | —H | —CH₃ | —CH₃ | —H | —CH₂CH₃ | —H | —CH₃ |
| 270 | —OH | —CH₂CH₃ | —C(O)H | —H | —CH₃ | —CH₃ | —CH₃ | —H | —H | —CH₃ |
| 271 | —OH | —CH₂CH₃ | —C(O)H | —H | —CH₃ | —CH₂CH₃ | —CH₃ | —H | —H | —CH₃ |
| 272 | —OH | —CH₂CH₃ | —C(O)H | —H | —CH₃ | —CH₃ | —CH₃ | —CH₃ | —H | —CH₃ |
| 273 | —OH | —CH₂CH₃ | —C(O)H | —H | —CH₃ | —CH₂CH₃ | —CH₃ | —CH₃ | —H | —CH₃ |
| 274 | —OH | —CH₂CH₃ | —C(O)H | —H | —CH₃ | —CH₃ | —CH₃ | —CH₂CH₃ | —H | —CH₃ |
| 275 | —OH | —CH₂CH₃ | —C(O)H | —H | —CH₃ | —CH₃ | —CH₂CH₃ | —H | —H | —CH₃ |
| 276 | —OH | —CH₂CH₃ | —C(O)H | —H | —CH₃ | —CH₃ | —CH₂CH₃ | —CH₃ | —H | —CH₃ |
| 277 | —CH₃ | —C(O)H | —OCH₃ | —H | —H | —CH₃ | —H | —H | —CH₃ | —CH₃ |
| 278 | —CH₃ | —C(O)H | —OCH₃ | —H | —H | —CH₃ | —H | —H | —CH₂CH₃ | —CH₃ |
| 279 | —CH₃ | —C(O)H | —OCH₃ | —H | —H | —CH₂CH₃ | —H | —H | —CH₃ | —CH₃ |
| 280 | —CH₃ | —C(O)H | —OCH₃ | —H | —CH₃ | —CH₃ | —H | —H | —CH₃ | —CH₃ |
| 281 | —CH₃ | —C(O)H | —OCH₃ | —H | —CH₃ | —CH₃ | —H | —H | —CH₂CH₃ | —CH₃ |
| 282 | —CH₃ | —C(O)H | —OCH₃ | —H | —CH₃ | —CH₂CH₃ | —H | —H | —CH₃ | —CH₃ |
| 283 | —CH₃ | —C(O)H | —OCH₃ | —H | —CH₃ | —CH₂CH₃ | —H | —H | —CH₃ | —CH₃ |
| 284 | —CH₃ | —C(O)H | —OCH₃ | —H | —CH₃ | —CH₃ | —H | —H | —H | —CH₃ |
| 285 | —CH₃ | —C(O)H | —OCH₃ | —H | —CH₃ | —CH₂CH₃ | —H | —H | —H | —CH₃ |
| 286 | —CH₂CH₃ | —C(O)H | —OCH₃ | —H | —H | —CH₃ | —H | —H | —CH₃ | —CH₃ |
| 287 | —CH₂CH₃ | —C(O)H | —OCH₃ | —H | —H | —CH₃ | —H | —H | —CH₂CH₃ | —CH₃ |
| 288 | —CH₂CH₃ | —C(O)H | —OCH₃ | —H | —H | —CH₂CH₃ | —H | —H | —CH₃ | —CH₃ |
| 289 | —CH₂CH₃ | —C(O)H | —OCH₃ | —H | —CH₃ | —CH₃ | —H | —H | —CH₃ | —CH₃ |
| 290 | —CH₂CH₃ | —C(O)H | —OCH₃ | —H | —CH₃ | —CH₃ | —H | —H | —CH₂CH₃ | —CH₃ |
| 291 | —CH₂CH₃ | —C(O)H | —OCH₃ | —H | —CH₃ | —CH₂CH₃ | —H | —H | —CH₃ | —CH₃ |
| 292 | —CH₂CH₃ | —C(O)H | —OCH₃ | —H | —CH₃ | —CH₂CH₃ | —H | —H | —CH₃ | —CH₃ |
| 293 | —CH₂CH₃ | —C(O)H | —OCH₃ | —H | —CH₃ | —CH₃ | —H | —H | —H | —CH₃ |
| 294 | —CH₂CH₃ | —C(O)H | —OCH₃ | —H | —CH₃ | —CH₂CH₃ | —H | —H | —H | —CH₃ |
| 295 | —CH₃ | —C(O)H | —OH | —H | —H | —CH₃ | —H | —H | —CH₃ | —CH₃ |
| 296 | —CH₃ | —C(O)H | —OH | —H | —H | —CH₃ | —H | —H | —CH₂CH₃ | —CH₃ |
| 297 | —CH₃ | —C(O)H | —OH | —H | —H | —CH₂CH₃ | —H | —H | —CH₃ | —CH₃ |
| 298 | —CH₃ | —C(O)H | —OH | —H | —CH₃ | —CH₃ | —H | —H | —CH₃ | —CH₃ |
| 299 | —CH₃ | —C(O)H | —OH | —H | —CH₃ | —CH₃ | —H | —H | —CH₂CH₃ | —CH₃ |
| 300 | —CH₃ | —C(O)H | —OH | —H | —CH₃ | —CH₂CH₃ | —H | —H | —CH₃ | —CH₃ |
| 301 | —CH₃ | —C(O)H | —OH | —H | —CH₃ | —CH₂CH₃ | —H | —H | —CH₃ | —CH₃ |
| 302 | —CH₃ | —C(O)H | —OH | —H | —CH₃ | —CH₃ | —H | —H | —H | —CH₃ |
| 303 | —CH₃ | —C(O)H | —OH | —H | —CH₃ | —CH₂CH₃ | —H | —H | —H | —CH₃ |
| 304 | —CH₂CH₃ | —C(O)H | —OH | —H | —H | —CH₃ | —H | —H | —CH₃ | —CH₃ |
| 305 | —CH₂CH₃ | —C(O)H | —OH | —H | —H | —CH₃ | —H | —H | —CH₂CH₃ | —CH₃ |
| 306 | —CH₂CH₃ | —C(O)H | —OH | —H | —H | —CH₂CH₃ | —H | —H | —CH₃ | —CH₃ |
| 307 | —CH₂CH₃ | —C(O)H | —OH | —H | —CH₃ | —CH₃ | —H | —H | —CH₃ | —CH₃ |
| 308 | —CH₂CH₃ | —C(O)H | —OH | —H | —CH₃ | —CH₃ | —H | —H | —CH₂CH₃ | —CH₃ |
| 309 | —CH₂CH₃ | —C(O)H | —OH | —H | —CH₃ | —CH₂CH₃ | —H | —H | —CH₃ | —CH₃ |
| 310 | —CH₂CH₃ | —C(O)H | —OH | —H | —CH₃ | —CH₂CH₃ | —H | —H | —CH₃ | —CH₃ |
| 311 | —CH₂CH₃ | —C(O)H | —OH | —H | —CH₃ | —CH₃ | —H | —H | —H | —CH₃ |
| 312 | —CH₂CH₃ | —C(O)H | —OH | —H | —CH₃ | —CH₂CH₃ | —H | —H | —H | —CH₃ |
| 313 | —OCH₃ | —C(O)H | —CH₃ | —H | —H | —CH₃ | —H | —H | —CH₃ | —CH₃ |
| 314 | —OCH₃ | —C(O)H | —CH₃ | —H | —H | —CH₃ | —H | —H | —CH₂CH₃ | —CH₃ |
| 315 | —OCH₃ | —C(O)H | —CH₃ | —H | —H | —CH₃ | —H | —CH₃ | —CH₃ | —CH₃ |
| 316 | —OCH₃ | —C(O)H | —CH₃ | —H | —H | —CH₃ | —H | —CH₃ | —CH₂CH₃ | —CH₃ |
| 317 | —OCH₃ | —C(O)H | —CH₃ | —H | —H | —CH₃ | —H | —CH₂CH₃ | —CH₃ | —CH₃ |
| 318 | —OCH₃ | —C(O)H | —CH₃ | —H | —H | —CH₃ | —CH₃ | —H | —CH₃ | —CH₃ |
| 319 | —OCH₃ | —C(O)H | —CH₃ | —H | —H | —CH₃ | —CH₃ | —H | —CH₂CH₃ | —CH₃ |
| 320 | —OCH₃ | —C(O)H | —CH₃ | —H | —H | —CH₃ | —CH₃ | —CH₃ | —CH₃ | —CH₃ |
| 321 | —OCH₃ | —C(O)H | —CH₃ | —H | —H | —CH₃ | —CH₃ | —CH₃ | —CH₂CH₃ | —CH₃ |
| 322 | —OCH₃ | —C(O)H | —CH₃ | —H | —H | —CH₃ | —CH₃ | —CH₂CH₃ | —CH₃ | —CH₃ |
| 323 | —OCH₃ | —C(O)H | —CH₃ | —H | —H | —CH₃ | —CH₂CH₃ | —H | —CH₃ | —CH₃ |
| 324 | —OCH₃ | —C(O)H | —CH₃ | —H | —H | —CH₃ | —CH₂CH₃ | —CH₃ | —CH₃ | —CH₃ |
| 325 | —OCH₃ | —C(O)H | —CH₃ | —H | —H | —CH₂CH₃ | —H | —H | —CH₃ | —CH₃ |
| 326 | —OCH₃ | —C(O)H | —CH₃ | —H | —H | —CH₂CH₃ | —H | —CH₃ | —CH₃ | —CH₃ |
| 327 | —OCH₃ | —C(O)H | —CH₃ | —H | —H | —CH₂CH₃ | —CH₃ | —H | —CH₃ | —CH₃ |
| 328 | —OCH₃ | —C(O)H | —CH₃ | —H | —H | —CH₂CH₃ | —CH₃ | —CH₃ | —CH₃ | —CH₃ |
| 329 | —OCH₃ | —C(O)H | —CH₃ | —H | —CH₃ | —CH₃ | —H | —CH₃ | —CH₃ | —CH₃ |
| 330 | —OCH₃ | —C(O)H | —CH₃ | —H | —CH₃ | —CH₃ | —H | —CH₃ | —CH₂CH₃ | —CH₃ |
| 331 | —OCH₃ | —C(O)H | —CH₃ | —H | —CH₃ | —CH₃ | —H | —CH₂CH₃ | —CH₃ | —CH₃ |
| 332 | —OCH₃ | —C(O)H | —CH₃ | —H | —CH₃ | —CH₃ | —CH₃ | —H | —CH₃ | —CH₃ |
| 333 | —OCH₃ | —C(O)H | —CH₃ | —H | —CH₃ | —CH₃ | —CH₃ | —H | —CH₂CH₃ | —CH₃ |
| 334 | —OCH₃ | —C(O)H | —CH₃ | —H | —CH₃ | —CH₃ | —CH₃ | —CH₃ | —CH₃ | —CH₃ |
| 335 | —OCH₃ | —C(O)H | —CH₃ | —H | —CH₃ | —CH₃ | —CH₃ | —CH₃ | —CH₂CH₃ | —CH₃ |
| 336 | —OCH₃ | —C(O)H | —CH₃ | —H | —CH₃ | —CH₃ | —CH₃ | —CH₂CH₃ | —CH₃ | —CH₃ |
| 337 | —OCH₃ | —C(O)H | —CH₃ | —H | —CH₃ | —CH₃ | —CH₂CH₃ | —H | —CH₃ | —CH₃ |
| 338 | —OCH₃ | —C(O)H | —CH₃ | —H | —CH₃ | —CH₃ | —CH₂CH₃ | —CH₃ | —CH₃ | —CH₃ |
| 339 | —OCH₃ | —C(O)H | —CH₃ | —H | —CH₃ | —CH₂CH₃ | —H | —H | —CH₃ | —CH₃ |
| 340 | —OCH₃ | —C(O)H | —CH₃ | —H | —CH₃ | —CH₂CH₃ | —H | —CH₃ | —CH₃ | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 341 | —OCH₃ | —C(O)H | —CH₃ | —H | —CH₃ | —CH₂CH₃ | —CH₃ | —H | —CH₃ | —CH₃ |
| 342 | —OCH₃ | —C(O)H | —CH₃ | —H | —CH₃ | —CH₂CH₃ | —CH₃ | —CH₃ | —CH₃ | —CH₃ |
| 343 | —OCH₃ | —C(O)H | —CH₃ | —H | —CH₃ | —CH₂CH₃ | —H | —H | —CH₃ | —CH₃ |
| 344 | —OCH₃ | —C(O)H | —CH₃ | —H | —CH₃ | —CH₂CH₃ | —H | —CH₃ | —CH₃ | —CH₃ |
| 345 | —OCH₃ | —C(O)H | —CH₃ | —H | —CH₃ | —CH₂CH₃ | —CH₃ | —H | —CH₃ | —CH₃ |
| 346 | —OCH₃ | —C(O)H | —CH₃ | —H | —CH₃ | —CH₂CH₃ | —CH₃ | —CH₃ | —CH₃ | —CH₃ |
| 347 | —OCH₃ | —C(O)H | —CH₃ | —H | —CH₃ | —CH₃ | —H | —H | —H | —CH₃ |
| 348 | —OCH₃ | —C(O)H | —CH₃ | —H | —CH₃ | —CH₂CH₃ | —H | —H | —H | —CH₃ |
| 349 | —OCH₃ | —C(O)H | —CH₃ | —H | —CH₃ | —CH₃ | —H | —CH₃ | —H | —CH₃ |
| 350 | —OCH₃ | —C(O)H | —CH₃ | —H | —CH₃ | —CH₂CH₃ | —H | —CH₃ | —H | —CH₃ |
| 351 | —OCH₃ | —C(O)H | —CH₃ | —H | —CH₃ | —CH₃ | —H | —CH₂CH₃ | —H | —CH₃ |
| 352 | —OCH₃ | —C(O)H | —CH₃ | —H | —CH₃ | —CH₃ | —CH₃ | —H | —H | —CH₃ |
| 353 | —OCH₃ | —C(O)H | —CH₃ | —H | —CH₃ | —CH₂CH₃ | —CH₃ | —H | —H | —CH₃ |
| 354 | —OCH₃ | —C(O)H | —CH₃ | —H | —CH₃ | —CH₃ | —CH₃ | —CH₃ | —H | —CH₃ |
| 355 | —OCH₃ | —C(O)H | —CH₃ | —H | —CH₃ | —CH₂CH₃ | —CH₃ | —CH₃ | —H | —CH₃ |
| 356 | —OCH₃ | —C(O)H | —CH₃ | —H | —CH₃ | —CH₃ | —CH₃ | —CH₂CH₃ | —H | —CH₃ |
| 357 | —OCH₃ | —C(O)H | —CH₃ | —H | —CH₃ | —CH₃ | —CH₂CH₃ | —H | —H | —CH₃ |
| 358 | —OCH₃ | —C(O)H | —CH₃ | —H | —CH₃ | —CH₃ | —CH₂CH₃ | —CH₃ | —H | —CH₃ |
| 359 | —OCH₃ | —C(O)H | —CH₂CH₃ | —H | —H | —CH₃ | —H | —H | —CH₃ | —CH₃ |
| 360 | —OCH₃ | —C(O)H | —CH₂CH₃ | —H | —H | —CH₃ | —H | —H | —CH₂CH₃ | —CH₃ |
| 361 | —OCH₃ | —C(O)H | —CH₂CH₃ | —H | —H | —CH₃ | —H | —CH₃ | —CH₃ | —CH₃ |
| 362 | —OCH₃ | —C(O)H | —CH₂CH₃ | —H | —H | —CH₃ | —H | —CH₃ | —CH₂CH₃ | —CH₃ |
| 363 | —OCH₃ | —C(O)H | —CH₂CH₃ | —H | —H | —CH₃ | —H | —CH₂CH₃ | —CH₃ | —CH₃ |
| 364 | —OCH₃ | —C(O)H | —CH₂CH₃ | —H | —H | —CH₃ | —CH₃ | —H | —CH₃ | —CH₃ |
| 365 | —OCH₃ | —C(O)H | —CH₂CH₃ | —H | —H | —CH₃ | —CH₃ | —H | —CH₂CH₃ | —CH₃ |
| 366 | —OCH₃ | —C(O)H | —CH₂CH₃ | —H | —H | —CH₃ | —CH₃ | —CH₃ | —CH₃ | —CH₃ |
| 367 | —OCH₃ | —C(O)H | —CH₂CH₃ | —H | —H | —CH₃ | —CH₃ | —CH₃ | —CH₂CH₃ | —CH₃ |
| 368 | —OCH₃ | —C(O)H | —CH₂CH₃ | —H | —H | —CH₃ | —CH₃ | —CH₂CH₃ | —CH₃ | —CH₃ |
| 369 | —OCH₃ | —C(O)H | —CH₂CH₃ | —H | —H | —CH₃ | —CH₂CH₃ | —H | —CH₃ | —CH₃ |
| 370 | —OCH₃ | —C(O)H | —CH₂CH₃ | —H | —H | —CH₃ | —CH₂CH₃ | —CH₃ | —CH₃ | —CH₃ |
| 371 | —OCH₃ | —C(O)H | —CH₂CH₃ | —H | —H | —CH₂CH₃ | —H | —H | —CH₃ | —CH₃ |
| 372 | —OCH₃ | —C(O)H | —CH₂CH₃ | —H | —H | —CH₂CH₃ | —H | —CH₃ | —CH₃ | —CH₃ |
| 373 | —OCH₃ | —C(O)H | —CH₂CH₃ | —H | —H | —CH₂CH₃ | —CH₃ | —H | —CH₃ | —CH₃ |
| 374 | —OCH₃ | —C(O)H | —CH₂CH₃ | —H | —H | —CH₂CH₃ | —CH₃ | —CH₃ | —CH₃ | —CH₃ |
| 375 | —OCH₃ | —C(O)H | —CH₂CH₃ | —H | —CH₃ | —CH₃ | —H | —H | —CH₂CH₃ | —CH₃ |
| 376 | —OCH₃ | —C(O)H | —CH₂CH₃ | —H | —CH₃ | —CH₃ | —H | —CH₃ | —CH₂CH₃ | —CH₃ |
| 377 | —OCH₃ | —C(O)H | —CH₂CH₃ | —H | —CH₃ | —CH₃ | —H | —CH₂CH₃ | —CH₃ | —CH₃ |
| 378 | —OCH₃ | —C(O)H | —CH₂CH₃ | —H | —CH₃ | —CH₃ | —CH₃ | —H | —CH₃ | —CH₃ |
| 379 | —OCH₃ | —C(O)H | —CH₂CH₃ | —H | —CH₃ | —CH₃ | —CH₃ | —H | —CH₂CH₃ | —CH₃ |
| 380 | —OCH₃ | —C(O)H | —CH₂CH₃ | —H | —CH₃ | —CH₃ | —CH₃ | —CH₃ | —CH₂CH₃ | —CH₃ |
| 381 | —OCH₃ | —C(O)H | —CH₂CH₃ | —H | —CH₃ | —CH₃ | —CH₃ | —CH₂CH₃ | —CH₃ | —CH₃ |
| 382 | —OCH₃ | —C(O)H | —CH₂CH₃ | —H | —CH₃ | —CH₃ | —CH₂CH₃ | —H | —CH₃ | —CH₃ |
| 383 | —OCH₃ | —C(O)H | —CH₂CH₃ | —H | —CH₃ | —CH₃ | —CH₂CH₃ | —CH₃ | —CH₃ | —CH₃ |
| 384 | —OCH₃ | —C(O)H | —CH₂CH₃ | —H | —CH₃ | —CH₂CH₃ | —H | —H | —CH₃ | —CH₃ |
| 385 | —OCH₃ | —C(O)H | —CH₂CH₃ | —H | —CH₃ | —CH₂CH₃ | —H | —CH₃ | —CH₃ | —CH₃ |
| 386 | —OCH₃ | —C(O)H | —CH₂CH₃ | —H | —CH₃ | —CH₂CH₃ | —CH₃ | —H | —CH₃ | —CH₃ |
| 387 | —OCH₃ | —C(O)H | —CH₂CH₃ | —H | —CH₃ | —CH₂CH₃ | —CH₃ | —CH₃ | —CH₃ | —CH₃ |
| 388 | —OCH₃ | —C(O)H | —CH₂CH₃ | —H | —CH₃ | —CH₂CH₃ | —H | —H | —CH₃ | —CH₃ |
| 389 | —OCH₃ | —C(O)H | —CH₂CH₃ | —H | —CH₃ | —CH₂CH₃ | —H | —CH₃ | —CH₃ | —CH₃ |
| 390 | —OCH₃ | —C(O)H | —CH₂CH₃ | —H | —CH₃ | —CH₂CH₃ | —CH₃ | —H | —CH₃ | —CH₃ |
| 391 | —OCH₃ | —C(O)H | —CH₂CH₃ | —H | —CH₃ | —CH₂CH₃ | —CH₃ | —CH₃ | —CH₃ | —CH₃ |
| 392 | —OCH₃ | —C(O)H | —CH₂CH₃ | —H | —CH₃ | —CH₃ | —H | —H | —H | —CH₃ |
| 393 | —OCH₃ | —C(O)H | —CH₂CH₃ | —H | —CH₃ | —CH₂CH₃ | —H | —H | —H | —CH₃ |
| 394 | —OCH₃ | —C(O)H | —CH₂CH₃ | —H | —CH₃ | —CH₃ | —H | —CH₃ | —H | —CH₃ |
| 395 | —OCH₃ | —C(O)H | —CH₂CH₃ | —H | —CH₃ | —CH₂CH₃ | —H | —CH₃ | —H | —CH₃ |
| 396 | —OCH₃ | —C(O)H | —CH₂CH₃ | —H | —CH₃ | —CH₃ | —H | —CH₂CH₃ | —H | —CH₃ |
| 397 | —OCH₃ | —C(O)H | —CH₂CH₃ | —H | —CH₃ | —CH₃ | —CH₃ | —H | —H | —CH₃ |
| 398 | —OCH₃ | —C(O)H | —CH₂CH₃ | —H | —CH₃ | —CH₂CH₃ | —CH₃ | —H | —H | —CH₃ |
| 399 | —OCH₃ | —C(O)H | —CH₂CH₃ | —H | —CH₃ | —CH₃ | —CH₃ | —CH₃ | —H | —CH₃ |
| 400 | —OCH₃ | —C(O)H | —CH₂CH₃ | —H | —CH₃ | —CH₂CH₃ | —CH₃ | —CH₃ | —H | —CH₃ |
| 401 | —OCH₃ | —C(O)H | —CH₂CH₃ | —H | —CH₃ | —CH₃ | —CH₃ | —CH₂CH₃ | —H | —CH₃ |
| 402 | —OCH₃ | —C(O)H | —CH₂CH₃ | —H | —CH₃ | —CH₃ | —CH₂CH₃ | —H | —H | —CH₃ |
| 403 | —OCH₃ | —C(O)H | —CH₂CH₃ | —H | —CH₃ | —CH₃ | —CH₂CH₃ | —CH₃ | —H | —CH₃ |
| 404 | —OCH₃ | —C(O)H | —OCH₃ | —H | —H | —CH₃ | —H | —H | —CH₃ | —CH₃ |
| 405 | —OCH₃ | —C(O)H | —OCH₃ | —H | —H | —CH₃ | —H | —H | —CH₂CH₃ | —CH₃ |
| 406 | —OCH₃ | —C(O)H | —OCH₃ | —H | —H | —CH₃ | —H | —CH₃ | —CH₃ | —CH₃ |
| 407 | —OCH₃ | —C(O)H | —OCH₃ | —H | —H | —CH₃ | —H | —CH₃ | —CH₂CH₃ | —CH₃ |
| 408 | —OCH₃ | —C(O)H | —OCH₃ | —H | —H | —CH₃ | —H | —CH₂CH₃ | —CH₃ | —CH₃ |
| 409 | —OCH₃ | —C(O)H | —OCH₃ | —H | —H | —CH₃ | —CH₃ | —H | —CH₃ | —CH₃ |
| 410 | —OCH₃ | —C(O)H | —OCH₃ | —H | —H | —CH₃ | —CH₃ | —H | —CH₂CH₃ | —CH₃ |
| 411 | —OCH₃ | —C(O)H | —OCH₃ | —H | —H | —CH₃ | —CH₃ | —CH₃ | —CH₃ | —CH₃ |
| 412 | —OCH₃ | —C(O)H | —OCH₃ | —H | —H | —CH₃ | —CH₃ | —CH₃ | —CH₂CH₃ | —CH₃ |
| 413 | —OCH₃ | —C(O)H | —OCH₃ | —H | —H | —CH₃ | —CH₃ | —CH₂CH₃ | —CH₃ | —CH₃ |
| 414 | —OCH₃ | —C(O)H | —OCH₃ | —H | —H | —CH₃ | —CH₂CH₃ | —H | —CH₃ | —CH₃ |
| 415 | —OCH₃ | —C(O)H | —OCH₃ | —H | —H | —CH₃ | —CH₂CH₃ | —CH₃ | —CH₃ | —CH₃ |
| 416 | —OCH₃ | —C(O)H | —OCH₃ | —H | —H | —CH₂CH₃ | —H | —H | —CH₃ | —CH₃ |
| 417 | —OCH₃ | —C(O)H | —OCH₃ | —H | —H | —CH₂CH₃ | —H | —CH₃ | —CH₃ | —CH₃ |
| 418 | —OCH₃ | —C(O)H | —OCH₃ | —H | —H | —CH₂CH₃ | —CH₃ | —H | —CH₃ | —CH₃ |
| 419 | —OCH₃ | —C(O)H | —OCH₃ | —H | —H | —CH₂CH₃ | —CH₃ | —CH₃ | —CH₃ | —CH₃ |
| 420 | —OCH₃ | —C(O)H | —OCH₃ | —H | —CH₃ | —CH₃ | —H | —H | —CH₂CH₃ | —CH₃ |
| 421 | —OCH₃ | —C(O)H | —OCH₃ | —H | —CH₃ | —CH₃ | —H | —CH₃ | —CH₃ | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 422 | —OCH₃ | —C(O)H | —OCH₃ | —H | —CH₃ | —CH₃ | —H | —CH₃ | —CH₂CH₃ | —CH₃ |
| 423 | —OCH₃ | —C(O)H | —OCH₃ | —H | —CH₃ | —CH₃ | —H | —CH₂CH₃ | —CH₃ | —CH₃ |
| 424 | —OCH₃ | —C(O)H | —OCH₃ | —H | —CH₃ | —CH₃ | —CH₃ | —H | —CH₂CH₃ | —CH₃ |
| 425 | —OCH₃ | —C(O)H | —OCH₃ | —H | —CH₃ | —CH₃ | —CH₃ | —CH₃ | —CH₃ | —CH₃ |
| 426 | —OCH₃ | —C(O)H | —OCH₃ | —H | —CH₃ | —CH₃ | —CH₃ | —CH₃ | —CH₂CH₃ | —CH₃ |
| 427 | —OCH₃ | —C(O)H | —OCH₃ | —H | —CH₃ | —CH₃ | —CH₃ | —CH₂CH₃ | —CH₃ | —CH₃ |
| 428 | —OCH₃ | —C(O)H | —OCH₃ | —H | —CH₃ | —CH₃ | —CH₂CH₃ | —H | —CH₃ | —CH₃ |
| 429 | —OCH₃ | —C(O)H | —OCH₃ | —H | —CH₃ | —CH₃ | —CH₂CH₃ | —CH₃ | —CH₃ | —CH₃ |
| 430 | —OCH₃ | —C(O)H | —OCH₃ | —H | —CH₃ | —CH₂CH₃ | —H | —H | —CH₃ | —CH₃ |
| 431 | —OCH₃ | —C(O)H | —OCH₃ | —H | —CH₃ | —CH₂CH₃ | —H | —CH₃ | —CH₃ | —CH₃ |
| 432 | —OCH₃ | —C(O)H | —OCH₃ | —H | —CH₃ | —CH₂CH₃ | —CH₃ | —H | —CH₃ | —CH₃ |
| 433 | —OCH₃ | —C(O)H | —OCH₃ | —H | —CH₃ | —CH₂CH₃ | —CH₃ | —CH₃ | —CH₃ | —CH₃ |
| 434 | —OCH₃ | —C(O)H | —OCH₃ | —H | —CH₃ | —CH₂CH₃ | —H | —H | —CH₃ | —CH₃ |
| 435 | —OCH₃ | —C(O)H | —OCH₃ | —H | —CH₃ | —CH₂CH₃ | —H | —CH₃ | —CH₃ | —CH₃ |
| 436 | —OCH₃ | —C(O)H | —OCH₃ | —H | —CH₃ | —CH₂CH₃ | —CH₃ | —H | —CH₃ | —CH₃ |
| 437 | —OCH₃ | —C(O)H | —OCH₃ | —H | —CH₃ | —CH₂CH₃ | —CH₃ | —CH₃ | —CH₃ | —CH₃ |
| 438 | —OCH₃ | —C(O)H | —OCH₃ | —H | —CH₃ | —CH₃ | —H | —H | —H | —CH₃ |
| 439 | —OCH₃ | —C(O)H | —OCH₃ | —H | —CH₃ | —CH₂CH₃ | —H | —H | —H | —CH₃ |
| 440 | —OCH₃ | —C(O)H | —OCH₃ | —H | —CH₃ | —CH₃ | —H | —CH₃ | —H | —CH₃ |
| 441 | —OCH₃ | —C(O)H | —OCH₃ | —H | —CH₃ | —CH₂CH₃ | —H | —CH₃ | —H | —CH₃ |
| 442 | —OCH₃ | —C(O)H | —OCH₃ | —H | —CH₃ | —CH₃ | —H | —CH₂CH₃ | —H | —CH₃ |
| 443 | —OCH₃ | —C(O)H | —OCH₃ | —H | —CH₃ | —CH₃ | —CH₃ | —H | —H | —CH₃ |
| 444 | —OCH₃ | —C(O)H | —OCH₃ | —H | —CH₃ | —CH₂CH₃ | —CH₃ | —H | —H | —CH₃ |
| 445 | —OCH₃ | —C(O)H | —OCH₃ | —H | —CH₃ | —CH₃ | —CH₃ | —CH₃ | —H | —CH₃ |
| 446 | —OCH₃ | —C(O)H | —OCH₃ | —H | —CH₃ | —CH₂CH₃ | —CH₃ | —CH₃ | —H | —CH₃ |
| 447 | —OCH₃ | —C(O)H | —OCH₃ | —H | —CH₃ | —CH₃ | —CH₃ | —CH₂CH₃ | —H | —CH₃ |
| 448 | —OCH₃ | —C(O)H | —OCH₃ | —H | —CH₃ | —CH₃ | —CH₂CH₃ | —H | —H | —CH₃ |
| 449 | —OCH₃ | —C(O)H | —OCH₃ | —H | —CH₃ | —CH₃ | —CH₂CH₃ | —CH₃ | —H | —CH₃ |
| 450 | —OH | —C(O)H | —CH₃ | —H | —H | —CH₃ | —H | —H | —CH₃ | —CH₃ |
| 451 | —OH | —C(O)H | —CH₃ | —H | —H | —CH₃ | —H | —H | —CH₂CH₃ | —CH₃ |
| 452 | —OH | —C(O)H | —CH₃ | —H | —H | —CH₃ | —H | —CH₃ | —CH₃ | —CH₃ |
| 453 | —OH | —C(O)H | —CH₃ | —H | —H | —CH₃ | —H | —CH₃ | —CH₂CH₃ | —CH₃ |
| 454 | —OH | —C(O)H | —CH₃ | —H | —H | —CH₃ | —H | —CH₂CH₃ | —CH₃ | —CH₃ |
| 455 | —OH | —C(O)H | —CH₃ | —H | —H | —CH₃ | —CH₃ | —H | —CH₃ | —CH₃ |
| 456 | —OH | —C(O)H | —CH₃ | —H | —H | —CH₃ | —CH₃ | —H | —CH₂CH₃ | —CH₃ |
| 457 | —OH | —C(O)H | —CH₃ | —H | —H | —CH₃ | —CH₃ | —CH₃ | —CH₃ | —CH₃ |
| 458 | —OH | —C(O)H | —CH₃ | —H | —H | —CH₃ | —CH₃ | —CH₃ | —CH₂CH₃ | —CH₃ |
| 459 | —OH | —C(O)H | —CH₃ | —H | —H | —CH₃ | —CH₃ | —CH₂CH₃ | —CH₃ | —CH₃ |
| 460 | —OH | —C(O)H | —CH₃ | —H | —H | —CH₃ | —CH₂CH₃ | —H | —CH₃ | —CH₃ |
| 461 | —OH | —C(O)H | —CH₃ | —H | —H | —CH₃ | —CH₂CH₃ | —CH₃ | —CH₃ | —CH₃ |
| 462 | —OH | —C(O)H | —CH₃ | —H | —H | —CH₂CH₃ | —H | —H | —CH₃ | —CH₃ |
| 463 | —OH | —C(O)H | —CH₃ | —H | —H | —CH₂CH₃ | —H | —CH₃ | —CH₃ | —CH₃ |
| 464 | —OH | —C(O)H | —CH₃ | —H | —H | —CH₂CH₃ | —CH₃ | —H | —CH₃ | —CH₃ |
| 465 | —OH | —C(O)H | —CH₃ | —H | —H | —CH₂CH₃ | —CH₃ | —CH₃ | —CH₃ | —CH₃ |
| 466 | —OH | —C(O)H | —CH₃ | —H | —CH₃ | —CH₃ | —H | —H | —CH₂CH₃ | —CH₃ |
| 467 | —OH | —C(O)H | —CH₃ | —H | —CH₃ | —CH₃ | —H | —CH₃ | —CH₃ | —CH₃ |
| 468 | —OH | —C(O)H | —CH₃ | —H | —CH₃ | —CH₃ | —H | —CH₃ | —CH₂CH₃ | —CH₃ |
| 469 | —OH | —C(O)H | —CH₃ | —H | —CH₃ | —CH₃ | —H | —CH₂CH₃ | —CH₃ | —CH₃ |
| 470 | —OH | —C(O)H | —CH₃ | —H | —CH₃ | —CH₃ | —CH₃ | —H | —CH₃ | —CH₃ |
| 471 | —OH | —C(O)H | —CH₃ | —H | —CH₃ | —CH₃ | —H | —CH₂CH₃ | —CH₃ | —CH₃ |
| 472 | —OH | —C(O)H | —CH₃ | —H | —CH₃ | —CH₃ | —CH₃ | —CH₃ | —CH₃ | —CH₃ |
| 473 | —OH | —C(O)H | —CH₃ | —H | —CH₃ | —CH₃ | —CH₃ | —CH₃ | —CH₂CH₃ | —CH₃ |
| 474 | —OH | —C(O)H | —CH₃ | —H | —CH₃ | —CH₃ | —CH₃ | —CH₂CH₃ | —CH₃ | —CH₃ |
| 475 | —OH | —C(O)H | —CH₃ | —H | —CH₃ | —CH₃ | —CH₂CH₃ | —H | —CH₃ | —CH₃ |
| 476 | —OH | —C(O)H | —CH₃ | —H | —CH₃ | —CH₃ | —CH₂CH₃ | —CH₃ | —CH₃ | —CH₃ |
| 477 | —OH | —C(O)H | —CH₃ | —H | —CH₃ | —CH₂CH₃ | —H | —H | —CH₃ | —CH₃ |
| 478 | —OH | —C(O)H | —CH₃ | —H | —CH₃ | —CH₂CH₃ | —H | —CH₃ | —CH₃ | —CH₃ |
| 479 | —OH | —C(O)H | —CH₃ | —H | —CH₃ | —CH₂CH₃ | —CH₃ | —H | —CH₃ | —CH₃ |
| 480 | —OH | —C(O)H | —CH₃ | —H | —CH₃ | —CH₂CH₃ | —CH₃ | —CH₃ | —CH₃ | —CH₃ |
| 481 | —OH | —C(O)H | —CH₃ | —H | —CH₃ | —CH₂CH₃ | —H | —H | —CH₃ | —CH₃ |
| 482 | —OH | —C(O)H | —CH₃ | —H | —CH₃ | —CH₂CH₃ | —H | —CH₃ | —CH₃ | —CH₃ |
| 483 | —OH | —C(O)H | —CH₃ | —H | —CH₃ | —CH₂CH₃ | —CH₃ | —H | —CH₃ | —CH₃ |
| 484 | —OH | —C(O)H | —CH₃ | —H | —CH₃ | —CH₂CH₃ | —CH₃ | —CH₃ | —CH₃ | —CH₃ |
| 485 | —OH | —C(O)H | —CH₃ | —H | —CH₃ | —CH₃ | —H | —H | —H | —CH₃ |
| 486 | —OH | —C(O)H | —CH₃ | —H | —CH₃ | —CH₂CH₃ | —H | —H | —H | —CH₃ |
| 487 | —OH | —C(O)H | —CH₃ | —H | —CH₃ | —CH₃ | —H | —CH₃ | —H | —CH₃ |
| 488 | —OH | —C(O)H | —CH₃ | —H | —CH₃ | —CH₂CH₃ | —H | —CH₃ | —H | —CH₃ |
| 489 | —OH | —C(O)H | —CH₃ | —H | —CH₃ | —CH₃ | —H | —CH₂CH₃ | —H | —CH₃ |
| 490 | —OH | —C(O)H | —CH₃ | —H | —CH₃ | —CH₃ | —CH₃ | —H | —H | —CH₃ |
| 491 | —OH | —C(O)H | —CH₃ | —H | —CH₃ | —CH₂CH₃ | —CH₃ | —H | —H | —CH₃ |
| 492 | —OH | —C(O)H | —CH₃ | —H | —CH₃ | —CH₃ | —CH₃ | —CH₃ | —H | —CH₃ |
| 493 | —OH | —C(O)H | —CH₃ | —H | —CH₃ | —CH₂CH₃ | —CH₃ | —CH₃ | —H | —CH₃ |
| 494 | —OH | —C(O)H | —CH₃ | —H | —CH₃ | —CH₃ | —CH₃ | —CH₂CH₃ | —H | —CH₃ |
| 495 | —OH | —C(O)H | —CH₃ | —H | —CH₃ | —CH₃ | —CH₂CH₃ | —H | —H | —CH₃ |
| 496 | —OH | —C(O)H | —CH₃ | —H | —CH₃ | —CH₃ | —CH₂CH₃ | —CH₃ | —H | —CH₃ |
| 497 | —OH | —C(O)H | —CH₂CH₃ | —H | —H | —CH₃ | —H | —H | —CH₃ | —CH₃ |
| 498 | —OH | —C(O)H | —CH₂CH₃ | —H | —H | —CH₃ | —H | —H | —CH₂CH₃ | —CH₃ |
| 499 | —OH | —C(O)H | —CH₂CH₃ | —H | —H | —CH₃ | —H | —CH₃ | —CH₃ | —CH₃ |
| 500 | —OH | —C(O)H | —CH₂CH₃ | —H | —H | —CH₃ | —H | —CH₃ | —CH₂CH₃ | —CH₃ |
| 501 | —OH | —C(O)H | —CH₂CH₃ | —H | —H | —CH₃ | —H | —CH₂CH₃ | —CH₃ | —CH₃ |
| 502 | —OH | —C(O)H | —CH₂CH₃ | —H | —H | —CH₃ | —CH₃ | —H | —CH₃ | —CH₃ |

TABLE I-continued

| Compound | R¹ | R² | R³ | R⁴ | R⁵ | R⁶ | R⁷ | R⁸ | R⁹ | R¹⁰ |
|---|---|---|---|---|---|---|---|---|---|---|
| 503 | —OH | —C(O)H | —CH₂CH₃ | —H | —H | —CH₃ | —CH₃ | —H | —CH₂CH₃ | —CH₃ |
| 504 | —OH | —C(O)H | —CH₂CH₃ | —H | —H | —CH₃ | —CH₃ | —CH₃ | —CH₃ | —CH₃ |
| 505 | —OH | —C(O)H | —CH₂CH₃ | —H | —H | —CH₃ | —CH₃ | —CH₃ | —CH₂CH₃ | —CH₃ |
| 506 | —OH | —C(O)H | —CH₂CH₃ | —H | —H | —CH₃ | —CH₃ | —CH₂CH₃ | —CH₃ | —CH₃ |
| 507 | —OH | —C(O)H | —CH₂CH₃ | —H | —H | —CH₃ | —CH₂CH₃ | —H | —CH₃ | —CH₃ |
| 508 | —OH | —C(O)H | —CH₂CH₃ | —H | —H | —CH₃ | —CH₂CH₃ | —CH₃ | —CH₃ | —CH₃ |
| 509 | —OH | —C(O)H | —CH₂CH₃ | —H | —H | —CH₂CH₃ | —H | —H | —CH₃ | —CH₃ |
| 510 | —OH | —C(O)H | —CH₂CH₃ | —H | —H | —CH₂CH₃ | —H | —CH₃ | —CH₃ | —CH₃ |
| 511 | —OH | —C(O)H | —CH₂CH₃ | —H | —H | —CH₂CH₃ | —CH₃ | —H | —CH₃ | —CH₃ |
| 512 | —OH | —C(O)H | —CH₂CH₃ | —H | —H | —CH₂CH₃ | —CH₃ | —CH₃ | —CH₃ | —CH₃ |
| 513 | —OH | —C(O)H | —CH₂CH₃ | —H | —CH₃ | —CH₃ | —H | —H | —CH₂CH₃ | —CH₃ |
| 514 | —OH | —C(O)H | —CH₂CH₃ | —H | —CH₃ | —CH₃ | —H | —CH₃ | —CH₃ | —CH₃ |
| 515 | —OH | —C(O)H | —CH₂CH₃ | —H | —CH₃ | —CH₃ | —H | —CH₃ | —CH₂CH₃ | —CH₃ |
| 516 | —OH | —C(O)H | —CH₂CH₃ | —H | —CH₃ | —CH₃ | —H | —CH₂CH₃ | —CH₃ | —CH₃ |
| 517 | —OH | —C(O)H | —CH₂CH₃ | —H | —CH₃ | —CH₃ | —CH₃ | —H | —CH₂CH₃ | —CH₃ |
| 518 | —OH | —C(O)H | —CH₂CH₃ | —H | —CH₃ | —CH₃ | —CH₃ | —H | —CH₂CH₃ | —CH₃ |
| 519 | —OH | —C(O)H | —CH₂CH₃ | —H | —CH₃ | —CH₃ | —CH₃ | —CH₃ | —CH₃ | —CH₃ |
| 520 | —OH | —C(O)H | —CH₂CH₃ | —H | —CH₃ | —CH₃ | —CH₃ | —CH₃ | —CH₂CH₃ | —CH₃ |
| 521 | —OH | —C(O)H | —CH₂CH₃ | —H | —CH₃ | —CH₃ | —CH₃ | —CH₂CH₃ | —CH₃ | —CH₃ |
| 522 | —OH | —C(O)H | —CH₂CH₃ | —H | —CH₃ | —CH₃ | —CH₂CH₃ | —H | —CH₃ | —CH₃ |
| 523 | —OH | —C(O)H | —CH₂CH₃ | —H | —CH₃ | —CH₃ | —CH₂CH₃ | —CH₃ | —CH₃ | —CH₃ |
| 524 | —OH | —C(O)H | —CH₂CH₃ | —H | —CH₃ | —CH₂CH₃ | —H | —H | —CH₃ | —CH₃ |
| 525 | —OH | —C(O)H | —CH₂CH₃ | —H | —CH₃ | —CH₂CH₃ | —H | —CH₃ | —CH₃ | —CH₃ |
| 526 | —OH | —C(O)H | —CH₂CH₃ | —H | —CH₃ | —CH₂CH₃ | —CH₃ | —H | —CH₃ | —CH₃ |
| 527 | —OH | —C(O)H | —CH₂CH₃ | —H | —CH₃ | —CH₂CH₃ | —CH₃ | —CH₃ | —CH₃ | —CH₃ |
| 528 | —OH | —C(O)H | —CH₂CH₃ | —H | —CH₃ | —CH₂CH₃ | —H | —H | —CH₃ | —CH₃ |
| 529 | —OH | —C(O)H | —CH₂CH₃ | —H | —CH₃ | —CH₂CH₃ | —H | —CH₃ | —CH₃ | —CH₃ |
| 530 | —OH | —C(O)H | —CH₂CH₃ | —H | —CH₃ | —CH₂CH₃ | —CH₃ | —H | —CH₃ | —CH₃ |
| 531 | —OH | —C(O)H | —CH₂CH₃ | —H | —CH₃ | —CH₂CH₃ | —CH₃ | —CH₃ | —CH₃ | —CH₃ |
| 532 | —OH | —C(O)H | —CH₂CH₃ | —H | —CH₃ | —CH₃ | —H | —H | —H | —CH₃ |
| 533 | —OH | —C(O)H | —CH₂CH₃ | —H | —CH₃ | —CH₂CH₃ | —H | —H | —H | —CH₃ |
| 534 | —OH | —C(O)H | —CH₂CH₃ | —H | —CH₃ | —CH₃ | —H | —CH₃ | —H | —CH₃ |
| 535 | —OH | —C(O)H | —CH₂CH₃ | —H | —CH₃ | —CH₂CH₃ | —H | —CH₃ | —H | —CH₃ |
| 536 | —OH | —C(O)H | —CH₂CH₃ | —H | —CH₃ | —CH₃ | —H | —CH₂CH₃ | —H | —CH₃ |
| 537 | —OH | —C(O)H | —CH₂CH₃ | —H | —CH₃ | —CH₃ | —CH₃ | —H | —H | —CH₃ |
| 538 | —OH | —C(O)H | —CH₂CH₃ | —H | —CH₃ | —CH₂CH₃ | —CH₃ | —H | —H | —CH₃ |
| 539 | —OH | —C(O)H | —CH₂CH₃ | —H | —CH₃ | —CH₃ | —CH₃ | —CH₃ | —H | —CH₃ |
| 540 | —OH | —C(O)H | —CH₂CH₃ | —H | —CH₃ | —CH₂CH₃ | —CH₃ | —CH₃ | —H | —CH₃ |
| 541 | —OH | —C(O)H | —CH₂CH₃ | —H | —CH₃ | —CH₃ | —CH₃ | —CH₂CH₃ | —H | —CH₃ |
| 542 | —OH | —C(O)H | —CH₂CH₃ | —H | —CH₃ | —CH₃ | —CH₂CH₃ | —H | —H | —CH₃ |
| 543 | —OH | —C(O)H | —CH₂CH₃ | —H | —CH₃ | —CH₃ | —CH₂CH₃ | —CH₃ | —H | —CH₃ |
| 544 | —OCH₃ | —CH₃ | —C(O)H | —(CH₂)₂— | | —CH₃ | —H | —H | —CH₃ | —CH₃ |
| 545 | —OCH₃ | —CH₃ | —C(O)H | —(CH₂)₂— | | —CH₃ | —H | —H | —CH₂CH₃ | —CH₃ |
| 546 | —OCH₃ | —CH₃ | —C(O)H | —(CH₂)₂— | | —CH₂CH₃ | —H | —H | —CH₃ | —CH₃ |
| 547 | —OCH₃ | —CH₂CH₃ | —C(O)H | —(CH₂)₂— | | —CH₃ | —H | —H | —CH₃ | —CH₃ |
| 548 | —OCH₃ | —CH₂CH₃ | —C(O)H | —(CH₂)₂— | | —CH₃ | —H | —H | —CH₂CH₃ | —CH₃ |
| 549 | —OCH₃ | —CH₂CH₃ | —C(O)H | —(CH₂)₂— | | —CH₂CH₃ | —H | —H | —CH₃ | —CH₃ |
| 550 | —OCH₃ | —OCH₃ | —C(O)H | —(CH₂)₂— | | —CH₃ | —H | —H | —CH₃ | —CH₃ |
| 551 | —OCH₃ | —OCH₃ | —C(O)H | —(CH₂)₂— | | —CH₃ | —H | —H | —CH₂CH₃ | —CH₃ |
| 552 | —OH | —CH₃ | —C(O)H | —(CH₂)₂— | | —CH₃ | —H | —H | —CH₃ | —CH₃ |
| 553 | —OH | —CH₃ | —C(O)H | —(CH₂)₂— | | —CH₃ | —H | —H | —CH₂CH₃ | —CH₃ |
| 554 | —OH | —CH₃ | —C(O)H | —(CH₂)₂— | | —CH₂CH₃ | —H | —H | —CH₃ | —CH₃ |
| 555 | —OH | —CH₂CH₃ | —C(O)H | —(CH₂)₂— | | —CH₃ | —H | —H | —CH₃ | —CH₃ |
| 556 | —OH | —CH₂CH₃ | —C(O)H | —(CH₂)₂— | | —CH₃ | —H | —H | —CH₂CH₃ | —CH₃ |
| 557 | —OH | —CH₂CH₃ | —C(O)H | —(CH₂)₂— | | —CH₂CH₃ | —H | —H | —CH₃ | —CH₃ |
| 558 | —OCH₃ | —C(O)H | —CH₃ | —(CH₂)₂— | | —CH₃ | —H | —H | —CH₃ | —CH₃ |
| 559 | —OCH₃ | —C(O)H | —CH₃ | —(CH₂)₂— | | —CH₃ | —H | —H | —CH₂CH₃ | —CH₃ |
| 560 | —OCH₃ | —C(O)H | —CH₃ | —(CH₂)₂— | | —CH₂CH₃ | —H | —H | —CH₃ | —CH₃ |
| 561 | —OCH₃ | —C(O)H | —CH₂CH₃ | —(CH₂)₂— | | —CH₃ | —H | —H | —CH₃ | —CH₃ |
| 562 | —OCH₃ | —C(O)H | —CH₂CH₃ | —(CH₂)₂— | | —CH₃ | —H | —H | —CH₂CH₃ | —CH₃ |
| 563 | —OCH₃ | —C(O)H | —CH₂CH₃ | —(CH₂)₂— | | —CH₂CH₃ | —H | —H | —CH₃ | —CH₃ |
| 564 | —OCH₃ | —C(O)H | —OCH₃ | —(CH₂)₂— | | —CH₃ | —H | —H | —CH₃ | —CH₃ |
| 565 | —OCH₃ | —C(O)H | —OCH₃ | —(CH₂)₂— | | —CH₃ | —H | —H | —CH₂CH₃ | —CH₃ |
| 566 | —OCH₃ | —C(O)H | —OCH₃ | —(CH₂)₂— | | —CH₂CH₃ | —H | —H | —CH₃ | —CH₃ |
| 567 | —OH | —C(O)H | —CH₃ | —(CH₂)₂— | | —CH₃ | —H | —H | —CH₃ | —CH₃ |
| 568 | —OH | —C(O)H | —CH₃ | —(CH₂)₂— | | —CH₃ | —H | —H | —CH₂CH₃ | —CH₃ |
| 569 | —OH | —C(O)H | —CH₃ | —(CH₂)₂— | | —CH₂CH₃ | —H | —H | —CH₃ | —CH₃ |
| 570 | —OH | —C(O)H | —CH₂CH₃ | —(CH₂)₂— | | —CH₃ | —H | —H | —CH₃ | —CH₃ |
| 571 | —OH | —C(O)H | —CH₂CH₃ | —(CH₂)₂— | | —CH₃ | —H | —H | —CH₂CH₃ | —CH₃ |
| 572 | —OH | —C(O)H | —CH₂CH₃ | —(CH₂)₂— | | —CH₂CH₃ | —H | —H | —CH₃ | —CH₃ |
| 573 | —OCH₃ | —CH₃ | —C(O)H | —H | —H | —(CH₂)₃— | | —H | —CH₃ | —CH₃ |
| 574 | —OCH₃ | —CH₃ | —C(O)H | —H | —H | —(CH₂)₃— | | —H | —CH₂CH₃ | —CH₃ |
| 575 | —OCH₃ | —CH₃ | —C(O)H | —H | —CH₃ | —(CH₂)₃— | | —H | —H | —CH₃ |
| 576 | —OCH₃ | —CH₃ | —C(O)H | —H | —CH₃ | —(CH₂)₃— | | —H | —CH₃ | —CH₃ |
| 577 | —OCH₃ | —CH₃ | —C(O)H | —H | —CH₃ | —(CH₂)₃— | | —H | —CH₂CH₃ | —CH₃ |
| 578 | —OCH₃ | —CH₃ | —C(O)H | —H | —CH₂CH₃ | —(CH₂)₃— | | —H | —H | —CH₃ |
| 579 | —OCH₃ | —CH₃ | —C(O)H | —H | —CH₂CH₃ | —(CH₂)₃— | | —H | —H | —CH₃ |
| 580 | —OH | —CH₃ | —C(O)H | —H | —H | —(CH₂)₃— | | —H | —CH₃ | —CH₃ |
| 581 | —OH | —CH₃ | —C(O)H | —H | —H | —(CH₂)₃— | | —H | —CH₂CH₃ | —CH₃ |
| 582 | —OH | —CH₃ | —C(O)H | —H | —CH₃ | —(CH₂)₃— | | —H | —H | —CH₃ |
| 583 | —OH | —CH₃ | —C(O)H | —H | —CH₃ | —(CH₂)₃— | | —H | —CH₃ | —CH₃ |

TABLE I-continued

| Compound | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 584 | —OH | —CH$_3$ | —C(O)H | —H | —CH$_3$ | | —(CH$_2$)$_3$— | —H | —CH$_2$CH$_3$ | —CH$_3$ |
| 585 | —OH | —CH$_3$ | —C(O)H | —H | —CH$_2$CH$_3$ | | —(CH$_2$)$_3$— | —H | —H | —CH$_3$ |
| 586 | —OH | —CH$_3$ | —C(O)H | —H | —CH$_2$CH$_3$ | | —(CH$_2$)$_3$— | —H | —CH$_3$ | —CH$_3$ |
| 587 | —OCH$_3$ | —CH$_2$CH$_3$ | —C(O)H | —H | —H | | —(CH$_2$)$_3$— | —H | —CH$_3$ | —CH$_3$ |
| 588 | —OCH$_3$ | —CH$_2$CH$_3$ | —C(O)H | —H | —H | | —(CH$_2$)$_3$— | —H | —CH$_2$CH$_3$ | —CH$_3$ |
| 589 | —OCH$_3$ | —CH$_2$CH$_3$ | —C(O)H | —H | —CH$_3$ | | —(CH$_2$)$_3$— | —H | —H | —CH$_3$ |
| 590 | —OCH$_3$ | —CH$_2$CH$_3$ | —C(O)H | —H | —CH$_3$ | | —(CH$_2$)$_3$— | —H | —CH$_3$ | —CH$_3$ |
| 591 | —OCH$_3$ | —CH$_2$CH$_3$ | —C(O)H | —H | —CH$_3$ | | —(CH$_2$)$_3$— | —H | —CH$_2$CH$_3$ | —CH$_3$ |
| 592 | —OCH$_3$ | —CH$_2$CH$_3$ | —C(O)H | —H | —CH$_2$CH$_3$ | | —(CH$_2$)$_3$— | —H | —H | —CH$_3$ |
| 593 | —OH | —CH$_2$CH$_3$ | —C(O)H | —H | —H | | —(CH$_2$)$_3$— | —H | —CH$_3$ | —CH$_3$ |
| 594 | —OH | —CH$_2$CH$_3$ | —C(O)H | —H | —H | | —(CH$_2$)$_3$— | —H | —CH$_2$CH$_3$ | —CH$_3$ |
| 595 | —OH | —CH$_2$CH$_3$ | —C(O)H | —H | —CH$_3$ | | —(CH$_2$)$_3$— | —H | —H | —CH$_3$ |
| 596 | —OH | —CH$_2$CH$_3$ | —C(O)H | —H | —CH$_3$ | | —(CH$_2$)$_3$— | —H | —CH$_3$ | —CH$_3$ |
| 597 | —OH | —CH$_2$CH$_3$ | —C(O)H | —H | —CH$_3$ | | —(CH$_2$)$_3$— | —H | —CH$_2$CH$_3$ | —CH$_3$ |
| 598 | —OH | —CH$_2$CH$_3$ | —C(O)H | —H | —CH$_2$CH$_3$ | | —(CH$_2$)$_3$— | —H | —H | —CH$_3$ |
| 599 | —OH | —CH$_2$CH$_3$ | —C(O)H | —H | —CH$_2$CH$_3$ | | —(CH$_2$)$_3$— | —H | —CH$_3$ | —CH$_3$ |
| 600 | —OCH$_3$ | —OCH$_3$ | —C(O)H | —H | —H | | —(CH$_2$)$_3$— | —H | —CH$_3$ | —CH$_3$ |
| 601 | —OCH$_3$ | —OCH$_3$ | —C(O)H | —H | —H | | —(CH$_2$)$_3$— | —H | —CH$_2$CH$_3$ | —CH$_3$ |
| 602 | —OCH$_3$ | —OCH$_3$ | —C(O)H | —H | —CH$_3$ | | —(CH$_2$)$_3$— | —H | —H | —CH$_3$ |
| 603 | —OCH$_3$ | —OCH$_3$ | —C(O)H | —H | —CH$_3$ | | —(CH$_2$)$_3$— | —H | —CH$_3$ | —CH$_3$ |
| 604 | —OCH$_3$ | —OCH$_3$ | —C(O)H | —H | —CH$_3$ | | —(CH$_2$)$_3$— | —H | —CH$_2$CH$_3$ | —CH$_3$ |
| 605 | —OCH$_3$ | —OCH$_3$ | —C(O)H | —H | —CH$_2$CH$_3$ | | —(CH$_2$)$_3$— | —H | —H | —CH$_3$ |
| 606 | —OCH$_3$ | —OCH$_3$ | —CH$_3$ | —H | —CH$_2$CH$_3$ | | —(CH$_2$)$_3$— | —H | —CH$_3$ | —CH$_3$ |
| 607 | —OCH$_3$ | —C(O)H | —CH$_3$ | —H | —H | | —(CH$_2$)$_3$— | —H | —CH$_3$ | —CH$_3$ |
| 608 | —OCH$_3$ | —C(O)H | —CH$_3$ | —H | —H | | —(CH$_2$)$_3$— | —H | —CH$_2$CH$_3$ | —CH$_3$ |
| 609 | —OCH$_3$ | —C(O)H | —CH$_3$ | —H | —CH$_3$ | | —(CH$_2$)$_3$— | —H | —H | —CH$_3$ |
| 610 | —OCH$_3$ | —C(O)H | —CH$_3$ | —H | —CH$_3$ | | —(CH$_2$)$_3$— | —H | —CH$_3$ | —CH$_3$ |
| 611 | —OCH$_3$ | —C(O)H | —CH$_3$ | —H | —CH$_3$ | | —(CH$_2$)$_3$— | —H | —CH$_2$CH$_3$ | —CH$_3$ |
| 612 | —OCH$_3$ | —C(O)H | —CH$_3$ | —H | —CH$_2$CH$_3$ | | —(CH$_2$)$_3$— | —H | —H | —CH$_3$ |
| 613 | —OCH$_3$ | —C(O)H | —CH$_3$ | —H | —CH$_2$CH$_3$ | | —(CH$_2$)$_3$— | —H | —CH$_3$ | —CH$_3$ |
| 614 | —OH | —C(O)H | —CH$_3$ | —H | —H | | —(CH$_2$)$_3$— | —H | —CH$_3$ | —CH$_3$ |
| 615 | —OH | —C(O)H | —CH$_3$ | —H | —H | | —(CH$_2$)$_3$— | —H | —CH$_2$CH$_3$ | —CH$_3$ |
| 616 | —OH | —C(O)H | —CH$_3$ | —H | —CH$_3$ | | —(CH$_2$)$_3$— | —H | —H | —CH$_3$ |
| 617 | —OH | —C(O)H | —CH$_3$ | —H | —CH$_3$ | | —(CH$_2$)$_3$— | —H | —CH$_3$ | —CH$_3$ |
| 618 | —OH | —C(O)H | —CH$_3$ | —H | —CH$_3$ | | —(CH$_2$)$_3$— | —H | —CH$_2$CH$_3$ | —CH$_3$ |
| 619 | —OH | —C(O)H | —CH$_3$ | —H | —CH$_2$CH$_3$ | | —(CH$_2$)$_3$— | —H | —H | —CH$_3$ |
| 620 | —OH | —C(O)H | —CH$_3$ | —H | —CH$_2$CH$_3$ | | —(CH$_2$)$_3$— | —H | —CH$_3$ | —CH$_3$ |
| 621 | —OCH$_3$ | —C(O)H | —CH$_2$CH$_3$ | —H | —H | | —(CH$_2$)$_3$— | —H | —CH$_3$ | —CH$_3$ |
| 622 | —OCH$_3$ | —C(O)H | —CH$_2$CH$_3$ | —H | —H | | —(CH$_2$)$_3$— | —H | —CH$_2$CH$_3$ | —CH$_3$ |
| 623 | —OCH$_3$ | —C(O)H | —CH$_2$CH$_3$ | —H | —CH$_3$ | | —(CH$_2$)$_3$— | —H | —H | —CH$_3$ |
| 624 | —OCH$_3$ | —C(O)H | —CH$_2$CH$_3$ | —H | —CH$_3$ | | —(CH$_2$)$_3$— | —H | —CH$_3$ | —CH$_3$ |
| 625 | —OCH$_3$ | —C(O)H | —CH$_2$CH$_3$ | —H | —CH$_3$ | | —(CH$_2$)$_3$— | —H | —CH$_2$CH$_3$ | —CH$_3$ |
| 626 | —OCH$_3$ | —C(O)H | —CH$_2$CH$_3$ | —H | —CH$_2$CH$_3$ | | —(CH$_2$)$_3$— | —H | —H | —CH$_3$ |
| 627 | —OCH$_3$ | —C(O)H | —CH$_2$CH$_3$ | —H | —CH$_2$CH$_3$ | | —(CH$_2$)$_3$— | —H | —CH$_3$ | —CH$_3$ |
| 628 | —OH | —C(O)H | —CH$_2$CH$_3$ | —H | —H | | —(CH$_2$)$_3$— | —H | —CH$_3$ | —CH$_3$ |
| 629 | —OH | —C(O)H | —CH$_2$CH$_3$ | —H | —H | | —(CH$_2$)$_3$— | —H | —CH$_2$CH$_3$ | —CH$_3$ |
| 630 | —OH | —C(O)H | —CH$_2$CH$_3$ | —H | —CH$_3$ | | —(CH$_2$)$_3$— | —H | —H | —CH$_3$ |
| 631 | —OH | —C(O)H | —CH$_2$CH$_3$ | —H | —CH$_3$ | | —(CH$_2$)$_3$— | —H | —CH$_3$ | —CH$_3$ |
| 632 | —OH | —C(O)H | —CH$_2$CH$_3$ | —H | —CH$_3$ | | —(CH$_2$)$_3$— | —H | —CH$_2$CH$_3$ | —CH$_3$ |
| 633 | —OH | —C(O)H | —CH$_2$CH$_3$ | —H | —CH$_2$CH$_3$ | | —(CH$_2$)$_3$— | —H | —H | —CH$_3$ |
| 634 | —OH | —C(O)H | —CH$_2$CH$_3$ | —H | —CH$_2$CH$_3$ | | —(CH$_2$)$_3$— | —H | —CH$_3$ | —CH$_3$ |
| 635 | —OCH$_3$ | —C(O)H | —OCH$_3$ | —H | —H | | —(CH$_2$)$_3$— | —H | —CH$_3$ | —CH$_3$ |
| 636 | —OCH$_3$ | —C(O)H | —OCH$_3$ | —H | —H | | —(CH$_2$)$_3$— | —H | —CH$_2$CH$_3$ | —CH$_3$ |
| 637 | —OCH$_3$ | —C(O)H | —OCH$_3$ | —H | —CH$_3$ | | —(CH$_2$)$_3$— | —H | —H | —CH$_3$ |
| 638 | —OCH$_3$ | —C(O)H | —OCH$_3$ | —H | —CH$_3$ | | —(CH$_2$)$_3$— | —H | —CH$_3$ | —CH$_3$ |
| 639 | —OCH$_3$ | —C(O)H | —OCH$_3$ | —H | —CH$_3$ | | —(CH$_2$)$_3$— | —H | —CH$_2$CH$_3$ | —CH$_3$ |
| 640 | —OCH$_3$ | —C(O)H | —OCH$_3$ | —H | —CH$_2$CH$_3$ | | —(CH$_2$)$_3$— | —H | —H | —CH$_3$ |
| 641 | —OCH$_3$ | —C(O)H | —OCH$_3$ | —H | —CH$_2$CH$_3$ | | —(CH$_2$)$_3$— | —H | —CH$_3$ | —CH$_3$ |

The novel alkyl tetralin aldehyde compounds of the present invention, with their musk aroma properties, have high utility in the fragrance industry. These compounds can be employed alone, in combination with one another, and/or in combination with one or more ingredients to provide excellent musk fragrance compositions. The compounds of the invention are particularly useful in rounding off compositions, and blend particularly well with aldehydes of various fragrance types.

For example, the compounds of Formula [I] may be used as olfactory components in anionic, cationic, nonionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the subject compounds to be used in modifying the olfactory or fragrance properties of a composition (that is, modifying, augmenting, enhancing, or improving the aroma of such compositions), will vary depending upon the particular use intended, as will be readily apparent to those skilled in the art. Although they may be present in major or minor amounts, preferably, because of the strength of their odor, the compounds of the invention are generally employed as a minor ingredient, that is, in an amount of about 0.1 percent by weight of the fragrance composition up to about 50 percent by weight of the fragrance composition, preferably about 0.1 percent by weight up to about 30 percent by weight of the fragrance composition, and most preferably about 0.1 percent by weight up to about 5.0 percent by weight of the fragrance composition. Within these basic parameters, the olfactorily effective amount (that is, the amount of the compounds of Formula [I] effective to modify, augment, enhance or improve the aroma properties of a composition) will be well within the ambit of one skilled in the art, once armed with the present disclosures.

The fragrance compositions of the invention may, if desired, contain a carrier or vehicle (as used herein, the term "carrier" shall be considered synonymous with the term "vehicle"). Such carriers include liquids such as a non-toxic alcohol, a non-toxic glycol, or the like. An example of a non-toxic alcohol is ethyl alcohol. An example of a non-toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular vehicle or carrier employed and use intended, as will be readily apparent to those skilled in the art. However, the vehicle or carrier can generally be employed in an amount of about 5 percent by weight up to about 95 percent by weight of the fragrance composition.

The fragrance composition may alternatively or additionally contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactures synthetically, as for example, alcohols such as geraniol, nerol, citronellol, linalol, tetrahydrogeraniol, beta-phenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aidehyde, vanillin or heliotropin; acetals derived from such aldehydes; ketones such as methyl hexyl ketone, the ionones and the methylionones; phenolic compounds such as eugenol and isoeugenol; other synthetic musks such as musk xylene, musk ketone, hexamethylisochroman, 5-acetylisopropyltetramethylidane, 6-acetyl-hexamethyltetralin (TETRALIDE®, a registered trademark of Bush Boake Allen Limited), 5-acetyl-hexamethylindane, and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in "Soap, Perfumery and Cosmetics", by W. A. Poucher, 7th edition, published by Chapman & Hall (London) (1959); "Perfume and Flavour Chemicals", by S. Arctander, published by the author (Montclair) (1959); and "Perfume and Flavour Materials of Natural Origin", also by S. Arctander, self-published (Elizabeth, N.J.) (1960), the disclosures of each of which are incorporated herein by reference, in their entirety.

This invention is further described in the following Examples 1–4, which illustrate methods of preparation for compounds of the invention. Examples 1–4 are prophetic examples. A summary of these examples is set forth below. These examples are intended to be illustrative only, and are not to be construed as limiting the scope of the appended claims.

Example 1 describes the preparation of 6-formyl-1,1,2,4,4,7-hexamethyl-5-methoxy-1,2,3,4-tetrahydronaphthalene, a compound of Formula I wherein $R^1$ is —$OCH_3$, $R^2$ is —$C(O)H$, $R^3$ is —$CH_3$, $R^4$ is —H, $R^5$ is —$CH_3$, $R^6$ is —$CH_3$, $R^7$ is —$CH_3$, $R^8$ is —H, $R^9$ is —$CH_3$ and $R^{10}$ is —$CH_3$.

Example 2 describes the preparation of 6-formyl-1,1,2,4,4,5-hexamethyl-7-methoxy-1,2,3,4-tetrahydronaphthalene, a compound of Formula I wherein $R^1$ is —$CH_3$, $R^2$ is —$C(O)H$, $R^3$ is —$OCH_3$, $R^4$ is —H, $R^5$ is —$CH_3$, $R^6$ is —$CH_3$, $R^7$ is —$CH_3$, $R^8$ is —H, $R^9$ is —$CH_3$ and $R^{10}$ is —$CH_3$.

Example 3 describes the preparation of 6-formyl-1,1,2,4,4-Pentamethyl-5,7-dimethoxy-1,2,3,4-tetrahydronaphthalene, a compound of Formula I wherein $R^1$ is —$OCH_3$, $R^2$ is —$C(O)H$, $R^3$ is —$OCH_3$, $R^4$ is —H, $R^5$ is —$CH_3$, $R^6$ is —$CH_3$, $R^7$ is —$CH_3$, $R^8$ is —H, $R^9$ is —$CH_3$ and $R^{10}$ is —$CH_3$.

Example 4 describes the preparation of 7-formyl-1,1,2,4,4-pentamethyl-5-methoxy-1,2,3,4-tetrahydronaphthalene, a compound of Formula I wherein $R^{10}$ is —$OCH_3$, $R^2$ is —H, $R^3$ is —$C(O)H$, $R^4$ is —H, $R^5$ is —$CH_3$, $R^6$ is —$CH_3$, $R^7$ is —$CH_3$, $R^8$ is —H, $R^9$ is —$CH_3$ and $R^{10}$ is —$CH_3$.

EXAMPLE 1

Preparation of
6-Formyl-1,1,2,4,4,7—Hexamethyl-5-Methoxy-1,2,3,4-Tetrahydronaphthalene Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methoxy-4-methyl-acetophenone (22.53 g). After about 2 hours, an aliquot of additional Grignard (20 ml) is added. The solution is then heated at 60° C. for about one hour, and quenched with aqueous $NH_4Cl$. The aqueous layer is then washed several times with methyl tert-butyl ether and rotoevaporated to yield a crude product mixture containing 1-[2'-methoxy-4'-methylphenyl]-1-methylethanol. The product mixture is then fractionated under reduced pressure to further purify the 1-[2'-methoxy-4'-methylphenyl]-1-methylethanol.

Next, 1-[2'-methoxy-4'-methylphenyl]-1-methylethanol is converted to 1,1,2,4,4,7-hexamethyl-5-methoxy-1,2,3,4-tetrahydronaphthalene by following procedures similar to those described in European Patent Application Publication No. 0,393,742. Specifically, to a stirred solution of 10 ml TiCl$_4$ in 120 ml dichloromethane (cooled to −5° C. under nitrogen), is added a mixture of 18.0 g of 1-[2'-methoxy-4'-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,7-hexamethyl-5-methoxy-1,2,3,4-tetrahydro-naphthalene. After removal of the solvent, the crude product may be further purified by fractional distillation under reduced pressure.

To convert 1,1,2,4,4,7-hexamethyl-5-methoxy-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.9 g of 1,1,2,4,4,7-hexamethyl-5-methoxy-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of 8° C. The solution is distilled to remove residual starting material to yield a crude product containing the 6-carboxaldehyde, 6-formyl-1,1,2,4,4,7-hexamethyl-5-methoxy-1,2,3,4-tetrahydronaphthalene. The crude product may then be further purified using further standard fractional distillation techniques.

EXAMPLE 2

Preparation of 6-Formyl-1,1,2,4,4,5-Hexamethyl-7-Methoxy-1,2,3,4-Tetrahydronaphthalene Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying, and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methyl-4-methoxy-acetophenone (22.53 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[4'-methoxy-2'-methylphenyl]-1-methylethanol. The product mixture is then fractionated under reduced pressure to further purify the 1-[4'-methoxy-2'-methylphenyl]-1-methylethanol.

Next, 1-[4'-methoxy-2'-methylphenyl]-1-methylethanol is converted to 1,1,2,4,4,5-hexamethyl-7-methoxy-1,2,3,4-tetrahydronaphthalene by following procedures similar to those described in European Patent Application Publication No. 0,393,742. Specifically, to a stirred solution of 10 ml TiCl$_4$ in 120 ml dichloromethane (cooled to −5° C. under nitrogen), is added a mixture of 18.0 g of 1-[4'-methoxy-2'-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,5-hexamethyl-7-methoxy-1,2,3,4-tetrahydro-naphthalene. After removal of the solvent, the crude product is further purified by fractional distillation under reduced pressure.

To convert 1,1,2,4,4,5-hexamethyl-7-methoxy-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.9 g of 1,1,2,4,4,5-hexamethyl-7-methoxy-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of 8° C. The solution is distilled to remove residual starting material to yield a crude product containing the 6-carboxaldehyde, 6-formyl-1,1,2,4,4,5-hexamethyl-7-methoxy-1,2,3,4-tetrahydronaphthalene. The crude product may then be further purified using further standard fractional distillation techniques.

EXAMPLE 3

Preparation of 6-Formyl-1,1,2,4,4-Pentamethyl-5,7-Dimethoxy-1,2,3,4-Tetrahydronaphthalene Using a Perrier modification, Perrier, *Chem. Ber.*, Vol. 33, pp. 819 et seq. (1900), and Perrier, *Bull. Soc. Chim. France*, pp. 859 et seq. (1904), 1,3-dimethoxybenzene (138.0 g) (which may be obtained from Aldrich Chemical Company, Inc., Milwaukee, Wis.) is reacted with acetyl chloride (72.0 g), methylene chloride (500 ml), and aluminum chloride (145 0 g) to provide 2',4'-dimethoxy-acetophenone, which may then be purified using standard vacuum fractional distillation.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2',4'-dimethoxy-acetophenone (24.73 g). After about 2 hours, an aliquot of additional Grignard (20 ml) is added. The solution is then heated at 60° C. for about one hour, and quenched with aqueous NH₄Cl. The aqueous layer is then washed several times with methyl tert-butyl ether and rotoevaporated to yield a crude product mixture containing 1-[2',4'-dimethoxyphenyl]-1-methylethanol. The product mixture is then fractionated under reduced pressure to further purify the 1-[2',4'-dimethoxyphenyl]-1-methylethanol Next, 1-[2',4'-dimethoxyphenyl]-1-methylethanol is converted to 1,1,2,4,4-pentamethyl-5,7-dimethoxy-1,2,3,4-tetrahydronaphthalene by following procedures similar to those described in European Patent Application Publication No. 0,393,742. Specifically, to a stirred solution of 10 ml TiCl₄ in 120 ml dichloromethane (cooled to −5° C. under nitrogen), is added a mixture of 19.61 g of 1-[2',4'-dimethoxyphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4-pentamethyl-5,7-dimethoxy-1,2,3,4-tetrahydronaphthalene. After removal of the solvent, the crude product Is further purified by fractional distillation under reduced pressure.

To convert 1,1,2,4,4-pentamethyl-5,7-dimethoxy-1,2,3,4-tetrahydronaphthalene to its corresponding 6-carboxaldehyde, a 250 ml flask is charged with 130 ml dichloromethane and 24.51 g TiCl₄. The solution is cooled to 2° C. and 15.87 g of 1,1,2,4,4-pentamethyl-5,7-dimethoxy-1,2,3,4-tetrahydronaphthalene and 20 ml dichloromethane are added with stirring. Then dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6-formyl-1,1,2,4,4-pentamethyl-5,7-dimethoxy-1,2,3,4-tetrahydronaphthalene. The crude product may then be further purified using further standard fractional distillation techniques.

EXAMPLE 4

Preparation of
7-Formyl-1,1,2,4,4-Pentamethyl-5-Methoxy-1,2,3,4-Tetrahydronaphthalene Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methoxy-4-methyl-acetophenone (22.53 g). After about 2 hours, an aliquot of additional Grignard (20 ml) is added. The solution is then heated at 60° C. for about one hour, and quenched with aqueous NH₄Cl. The aqueous layer is then washed several times with methyl tert-butyl ether and rotoevaporated to yield a crude product mixture containing 1-[2'-methoxy-4'-methylphenyl]-1-methylethanol. The product mixture is then fractionated under reduced pressure to further purify the 1-[2'-methoxy-4'-methylphenyl]-1-methylethanol.

Next, 1-[2'-methoxy-4'-methylphenyl]-1-methylethanol is converted to 1,1,2,4,4,7-hexamethyl-5-methoxy-1,2,3,4-tetrahydronaphthalene by following procedures similar to those described in European Patent Application Publication No. 0,393,742. Specifically, to a stirred solution of 10 ml TiCl₄ in 120 ml dichloromethane (cooled to −5° C. under nitrogen), is added a mixture of 18.0 g of 1-[2'-methoxy-4'-methylphenyl]-1-methylethanol and 16.8 g 2,3-dimethylbut-1-ene over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,7-hexamethyl-5-methoxy-1,2,3,4-tetrahydro-naphthalene. After removal of the solvent, the crude product is further purified by fractional distillation under reduced pressure.

To convert 1,1,2,4,4,7-hexamethyl-5-methoxy-1,2,3,4-tetrahydronaphthalene to 7-formyl-1,1,2,4,4-pentamethyl-5-methoxy-1,2,3,4-tetrahydronaphthalene, the oxidation procedures of Syper, Tetrahedron Letters, No. 37, pp. 4493-4498 (1966) are substantially followed. Specifically, to a solution of 14.8 g of 1,1,2,4,4,7-hexamethyl-5-methoxy-1,2,3,4-tetrahydronaphthalene in 300 ml of 50% aqueous acetic acid is prepared. While stirring, to this is added dropwise a solution of 131.5 g ceric ammonium nitrate in the same acid (600 ml), at 100° C. The solution is then cooled to room temperature, diluted with water, extracted three times with ether, and dried with MgSO₄, to yield the 7-carboxaldehyde, 7-formyl-1,1,2,4,4-pentamethyl-5-methoxy-1,2,3,4-tetrahydronaphthalene.

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A compound of the formula:

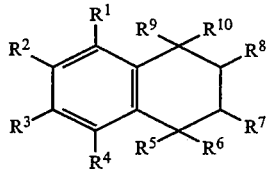 (I)

wherein
$R^1$ is —CH$_3$, —CH$_2$CH$_3$, —OCH$_3$ or —OH,
$R^2$ and $R^3$ are, independently, —H, —CH$_3$, —CH$_2$CH$_3$, —OCH$_3$, —OH or —C(O)H,
$R^4$ is —H,
$R^5$ is —H, —CH$_3$ or —CH$_2$CH$_3$,
or $R^4$ and $R^5$, taken together, are —(CH$_2$)$_2$—,
$R^6$ is —CH$_3$ or —CH$_2$CH$_3$,
$R^7$ is —H, —CH$_3$ or —CH$_2$CH$_3$,
or $R^6$ and $R^7$, taken together, are —(CH$_2$)$_3$—,
$R^8$ and $R^9$ are, independently, —H, —CH$_3$ or —CH$_2$CH$_3$, and
$R^{10}$ is —CH$_3$,
provided that
  (i) one of $R^2$ and $R^3$ is —C(O)H, and one of $R^2$ and $R^3$ is other than —C(O)H,
  (ii) no more than one of $R^5$ and $R^9$ is —H,
  (iii) no more than one of $R^5$, $R^6$, $R^7$, $R^8$ and $R^9$ is —CH$_2$CH$_3$,
  (iv) when $R^1$ is —OCH$_3$, then $R^2$ and $R^3$ are other than —H or —OH,
  (v) when $R^1$ is —OH, then $R^2$ and $R^3$ are other than —OH or —OCH$_3$,
  (vi) when $R^1$ is —CH$_3$ or —CH$_2$CH$_3$, then at least one of $R^7$ and $R^8$ are H,
  (vii) when $R^4$ and $R^5$, taken together, are —(CH$_2$)$_2$—, then $R^1$ is —OCH$_3$ or —OH, $R^7$ is —H, and $R^8$ is —H,
  (viii) when $R^6$ and $R^7$, taken together, are —(CH$_2$)$_3$—, then $R^1$ is —OCH$_3$ or —OH, and $R^8$ is —H,
  when $R^1$ is —CH$_3$ or —CH$_2$CH$_3$, then one of $R^2$ and $R^3$ is —OCH$_3$ or —OH; and
  when $R^1$ is —OCH$_3$ or —OH, $R^3$ is —CH$_3$ or —CH$_2$CH$_3$, and both $R^7$ and $R^8$ are —H, then at least one of $R^5$, $R^6$ and $R^9$ is other than —CH$_3$.

2. A compound of claim 1 wherein $R^1$ is —CH$_3$, —OH or —OCH$_3$.

3. A compound of claim 1 wherein $R^2$ is —C(O)H.

4. A compound of claim 1 wherein $R^3$ is —CH$_3$ or —CH$_2$CH$_3$.

5. A compound of claim 1 wherein $R^1$ is —OH or —OCH$_3$, $R^2$ is —C(O)H, $R^3$ is —CH$_3$ or —CH$_2$CH$_3$, $R^4$ is —H, $R^5$ is —CH$_3$, $R^6$ is —CH$_3$, $R^7$ is —H or —CH$_3$, $R^8$ is —H or —CH$_3$, $R^9$ is —CH$_3$, and $R^{10}$ is —CH$_3$.

6. A compound of claim 1 wherein $R^1$ is —OH or —OCH$_3$, $R^3$ is —C(O)H, $R^3$ is —CH$_3$, $R^4$ and $R^5$, taken together are —(CH$_2$)$_2$—, is —CH$_3$, $R^7$ is —H, $R^8$ is —H, $R^9$ is —CH$_3$, and $R^{10}$ is —CH$_3$.

7. A compound of claim 1 wherein $R^1$ is —OH or —OCH$_3$, $R^2$ is —C(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$.

8. A compound of claim 1 wherein $R^1$ is —OCH$_3$, $R^2$ is —C(O)H, $R^3$ is —CH$_3$, $R^4$ is —H, $R^5$ is —CH$_3$, $R^6$ is —CH$_3$, $R^7$ is —H, $R^8$ is —CH$_3$, $R^9$ is —CH$_3$, and $R^{10}$ is —CH$_3$.

9. A compound of claim 1 wherein $R^1$ is —OCH$_3$, $R^2$ is —C(O)H, $R^3$ is —OCH$_3$, $R^4$ is —H, $R^5$ is —CH$_3$, $R^6$ is —CH$_3$, $R^7$ is —H, $R^8$ is —H, $R^9$ is —CH$_3$, and $R^{10}$ is —CH$_3$.

10. A compound of claim 1 wherein $R^1$ is —OCH$_3$, $R^2$ is —C(O)H, $R^3$ is —OCH$_3$, $R^4$ is —H, $R^5$ is —CH$_3$, $R^6$ is —CH$_3$, $R^7$ is —CH$_3$, $R^8$ is —H, $R^9$ is —CH$_3$ and $R^{10}$ is —CH$_3$.

11. A compound of claim 1 wherein $R^1$ is —OCH$_3$, $R^2$ is —H, $R^3$ is —C(O)H, $R^4$ is —H, $R^5$ is —CH$_3$, $R^6$ is —CH$_3$, $R^7$ is —CH$_3$, $R^8$ is —H, $R^9$ is —CH$_3$ and $R^{10}$ is —CH$_3$.

12. A compound of claim 1 wherein $R^1$ is —OCH$_3$, $R^2$ is —C(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$.

13. A compound of claim 1 wherein $R^1$ is —OCH$_3$, $R^2$ is —C(O)H, $R^3$ is —CH$_2$CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$.

14. A compound of claim 1 wherein $R^1$ is —OH, $R^2$ is —C(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$.

15. A compound of claim 1 wherein $R^1$ is —OH, $R^2$ is —C(O)H, $R^3$ is —CH$_2$CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$.

16. A fragrance composition comprising a compound of claim 1 in combination with at least one of a carrier and additional perfumery material.

17. A fragrance composition comprising a compound of claim 9 in combination with at least one of a carrier and additional perfumery material.

18. A fragrance composition comprising a compound of claim 11 in combination with at least one of a carrier and additional perfumery material.

19. A fragrance composition comprising a compound of claim 13 in combination with at least one of a carrier and additional perfumery material.

20. A method of modifying the olfactory properties of a composition comprising adding thereto an olfactorily effective amount of a compound of claim 1.

21. A method of modifying the olfactory properties of a composition comprising adding thereto an olfactorily effective amount of a compound of claim 9.

22. A method of modifying the olfactory properties of a composition comprising adding thereto an olfactorily effective amount of a compound of claim 11.

23. A method of modifying the olfactory properties of a composition comprising adding thereto an olfactorily effective amount of a compound of claim 13.

* * * * *

UNITED STATES PATENT AND TRADEMARK OFFICE
CERTIFICATE OF CORRECTION

PATENT NO.  : 5,401,720
DATED       : March 28, 1995
INVENTOR(S) : Walter C. Frank It is certified that error appears in the above-indentified patent and that said Letters Patent is hereby corrected as shown below:

Column 31, line 40, insert --(ix)-- before "when".

Column 31, line 42, insert --(x)-- before "when".

Column 31, line 44, insert a space after "$R^6$".

Column 31, line 56, after "-$OCH_3$," delete "$R^3$" and insert --$R^2$--.

Column 31, line 57, insert --,-- after "together", after "-$(CH_2)_2$-," insert --$R^6$--, and after "$R^8$" insert a space.

Signed and Sealed this

Eighteenth Day of July, 1995

Attest:

BRUCE LEHMAN

Attesting Officer    Commissioner of Patents and Trademarks